United States Patent
Doi

(10) Patent No.: US 6,217,741 B1
(45) Date of Patent: *Apr. 17, 2001

(54) METHOD FOR MANUFACTURING BACTERICIDE

(75) Inventor: Toyohiko Doi, Higashiyamato (JP)

(73) Assignees: Morinaga Engineering Co., Ltd.; Morinaga Milk Industry Co., Ltd., both of Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,284

(22) Filed: Oct. 13, 1998

(51) Int. Cl.$^7$ ....................................... C25C 1/02
(52) U.S. Cl. .......................... 205/620; 205/701; 205/742
(58) Field of Search ................................... 205/701, 742, 205/620

(56) References Cited

U.S. PATENT DOCUMENTS

| 3,479,275 | 11/1969 | Gwynn et al. |
| 3,616,355 | 10/1971 | Themy et al. |
| 4,236,992 | * 12/1980 | Themy ................................ 204/278 |

FOREIGN PATENT DOCUMENTS

| 0 802 164 A1 | * 10/1997 | (EP) |
| 43-8230 | 3/1968 | (JP) |
| 63-16093 | 1/1988 | (JP) |
| 3-33332 | 2/1991 | (JP) |
| 4-94785 | 3/1992 | (JP) |
| 4-99295 | 3/1992 | (JP) |
| 5-50068 | 3/1993 | (JP) |
| 5-87489 | 4/1993 | (JP) |
| 7-218062 | 8/1995 | (JP) |
| 7-256262 | 10/1995 | (JP) |
| 8-229564 | 9/1996 | (JP) |
| 9-91124 | 4/1997 | (JP) |
| WO 97/17298 | 5/1997 | (JP) |

OTHER PUBLICATIONS

Atarashii Mizu no Kagaku to Riyogijutsu (New Science of Water and Technology applying thereof); pp. 200–207, Science Forum Sha (1992), No Month Available.

Japan Soda Industry Association, Soda and Chlorine, vol. 26, No. 4, p. 112, 1975, No Month Available.

* cited by examiner

Primary Examiner—Kathryn Gorgos
Assistant Examiner—Wesley A. Nicolas
(74) Attorney, Agent, or Firm—Oblon, Spivak, McClelland, Maier & Neustadt, P.C.

(57) ABSTRACT

The present invention relates to a method for manufacturing a novel bactericide consisting of an electrolytically treated liquid having high bactericidal action prepared from raw water by using electrolysis, wherein less electric power and water are required, the structure of the apparatus used therefore is a small scale, simple, and can be operated for long periods of time, and can reduce the manufacturing costs. The invention further relates to the apparatus for manufacturing the same, the bactericide that is manufactured by such a method, and a sterilizing method. The present invention also relates to a method for manufacturing a bactericide consisting of an electrolytically treated liquid having high bactericidal action, comprising introducing raw water containing hydrochloric acid into an electrolytic cell without a diaphragm between the cathode and anode, applying electric current between the cathode and anode immersed in the raw water containing the hydrochloric acid to electrolyze the raw water containing the hydrochloric acid, and then recovering the liquid thus electrolytically treated. The invention further relates to an apparatus for manufacturing the same, the bactericide that is manufactured by this method, and a method for sterilizing raw water.

3 Claims, 10 Drawing Sheets

METHOD FOR MANUFACTURING BACTERICIDE

BACKGROUND OF THE INVENTION

1. Field of the Invention

The present invention relates to a method for manufacturing a bactericide consisting of an electrolytically treated liquid having high bactericidal action, prepared by the electrolysis (hereinafter sometimes referred to as electrolytic treatment) of raw water containing hydrochloric acid, as well as to an apparatus for manufacturing the same, the bactericide that has been manufactured by this method, and a method for sterilizing raw water.

More specifically, the present invention relates to a method for manufacturing a bactericide comprising an electrolytically treated liquid having high bactericidal action, prepared by electrolyzing raw water containing hydrochloric acid by means of an electrolytic cell with no diaphragm between the cathode and anode, and recovering the electrolytically treated liquid without separating it into anode water and cathode water. The invention further relates to an apparatus for manufacturing the same, the bactericide that is manufactured by this method, and a method for sterilizing raw water using this method.

In the specification, percentages are weight percent unless otherwise specified.

2. Discussion of Background

In the present invention, "electric power efficiency" means the amount of chlorine being generated per unit consumption electric power, a value obtainable by dividing the amount of chlorine being generated in an electrolytic cell by electric power consumed in the electrolytic cell.

Methods for obtaining acidic water or alkali ion water by the electrolysis of water have been known in general. Electrolytic cells are generally used when water is electrolyzed for the purpose of obtaining acidic water or alkali ion water (under the editorial supervision of Kunihiko Watanuki et al, Atarashii Mizu no Kagaku to Riyogijutsu, pp. 200–207, Science Forum Sha. (1992)). Conventional electrolytic cells are equipped with an anode and cathode in the interior and have a dual-structure in which the anode and cathode are separated by a diaphragm to divide the cell into an anode chamber and cathode chamber, and the electrolysis of water is performed by supplying water containing a small amount of an electrolyte such as common salt to increase the electrical conductivity to the electrolytic cell, and applying direct current to the electrodes to electrolyze the water.

The action of a conventional electrolytic cell is described. Water as the object of the electrolysis (hereinafter referred to as raw water) is first supplied by a pump or the like to the anode and cathode chambers of the electrolytic cell and is electrolyzed, but since in the anode chamber the raw water is subject to oxidation action, resulting in the removal of part of the hydrochloric acid ions in the form of oxygen gas, the water discharged from the anode chamber has high redox potential and is acidic, resulting in so-called acidic water. In the cathode chamber, on the other hand, the raw water is subject to reducing action, resulting in the removal of part of the hydrogen ions in the form of hydrogen gas, so the water discharged from the cathode chamber has low redox potential and is alkaline, resulting in so-called alkali ion water. The acidic water has bactericidal action and is used to disinfect and wash utensils, hands, and the like in the workplace in the food product industry, medical industry, and the like, while the alkali ion water is used for drinking.

Acidic water having bactericidal action has thus been produced by electrolytic treatment in recent years, and this water has been used as a type of bactericide.

Meanwhile, the various types of raw water used in our daily lives, factory equipment, and the like often need to be sterilized, therefore there has always been a desire for a more effective method of sterilization, and the above conventional electrolytic cells accordingly have been used for that purpose.

For example, with respect to cooling water, which is circulated between the condenser of cooling equipment in plants and the like and the cooling tower to which the condenser belongs so as to effect heat exchange, germs tend to proliferate in such cooling water, posing health problems. As such, a method for preventing such germs from proliferating by setting up an electrolytic cell in the piping through which the cooling water circulates has been adopted (see, for example, Japanese Patent Gazette for Laid-Open Patent Publication No. 5-87489 (1993)). A method for treating the water flushing through the toilet by using cisterns of flush toilets equipped with an electrolytic cell has been reported (see, for example, Japanese Patent Gazette for Laid-Open Patent Publication No. 3-33332 (1991)), and a method for utilizing water that has been electrolytically treated by an electrolytic cell has been frozen for use in the form of ice has been reported (see, for example, Japanese Patent Gazette for Laid-Open Patent Publication No. 7-218062 (1995)). In other known techniques, a method for sterilizing the stored water by using electrolytic cells set up in baths, pools, and the like has been reported (see, for example, Japanese Patent Gazette for Laid-Open Patent Publication No. 7-256262 (1995)).

Various techniques have been proposed for modifying the conventional method of electrolytic treatment described above (hereinafter referred to as Conventional Technique 1). For example, there have been reports relating to techniques which make good use of the water on the unused side of the acidic water or alkali ion water during the electrolytic treatment. The following conventional techniques are also known as techniques for mitigating scale on the cathode. That is, a method which comprises using means for exchangeably adding an alkali neutralizer or acidic neutralizer set up in the cathode and anode chambers of the electrolytic cell, and neutralizing the unused one of the resulting acidic water or alkali ion water, mixing it with the other, and a method for preventing scale on the cathode by reversing the polarity of the electrodes in the electrolytic cell at appropriate times to reverse the functions of the cathode and anode chambers are reported (see Japanese Patent Gazette for Laid-Open Patent Publication No. 4-99295 (1992); Conventional Technique 2).

The inventors earlier developed the following technique to remedy such problems, and have already filed for a patent. That is, they completed a technique which comprises adding hydrochloric acid to raw water in the cathode camber of the electrolytic cell to render the water acidic in advance, producing nearly neutral alkali ion water in the cathode chamber, and feeding back this water to the raw water (Japanese Patent Application No. 7-63384 (1995); Conventional Technique 3).

In another known technique, a method which comprises preparing raw water filtered, adding salt to the water, electrolyzing the water by a common method to obtain acidic water with pH of 1.5 to 3.3, and using this water as a bactericide (Japanese Patent Application No. 7-274921 (1995); Conventional Technique 4).

As another known technique can be mentioned a technique comprising electrolyzing a chlorine ion-containing liquid by a voltage of at least 10 volts to generate ozone together with chlorine and employing them for a bactericide (U.S. Pat. No. 3,616,355; Conventional Technique 5).

The Conventional Technique 1 described above suffers from the following problems, however.

1) Calcium and the like which are dissolved in the raw water adhere to form scale on the surface of the cathode and compromise the efficiency of the electrolytic treatment, making long-term operation difficult.

2) The diaphragm exposed to acid and alkali on both sides and electrified result in considerable wear and high running costs.

3) When only the acidic water is desired for use as a bactericide, the alkali ion water is discarded, and the water and electric power used for the alkali ion water are thus wasted.

In the aforementioned Conventional Technique 2, on the other hand, the method of reversing the functions of the cathode and anode in the electrolytic cell has been adopted to mitigate the problem described in 1) above, but a drawback is that the extra device for reversing the electrodes is required. In order to alleviate the problem in 3) above, a method for neutralizing the unused alkali ion water with an acid so as to reuse it has been considered, but since this water is merely prepared by adjusting the pH alone, thus obtained water has drawbacks in that other properties such as the redox potential are compromised, preventing the inherent effects from being obtained.

In Conventional Technique 3 described above, there is a disadvantage that problem 2) in the aforementioned conventional techniques, that is, the expensive running costs, cannot be remedied.

In Conventional Technique 4 described above, alkali ion water is produced at the same time as acidic water (bactericide), resulting in considerable expenditure of electric power and water, large quantities of electric power are required to obtain acidic water of low pH from neutral raw water, resulting in the high overall running costs, and equipment for filtering the raw water is also needed to prevent scale on the cathode and the like, tending to result in a complicated apparatus.

Conventional Technique 5 has the following problems a) to c) since it comprises generating ozone together with chlorine and utilizing them for sterilization:

a) The bactericidal action of chlorine is durable for a long period of time, but that of ozone decreases rapidly. Hence, in the case where the bactericidal action of a bactericide depends also upon the bactericidal action of ozone as in Convention Technique 5, the bactericidal action decreases in a short time and it is difficult to secure a stable bactericidal action.

b) Since oxygen is also generated simultaneously at the time of generating ozone, electric power for generating oxygen is wasteful.

c) Since ozone is hard to dissolve in water as compared with chlorine, it is easily diffused into the air, and a countermeasure such that ozone diffused into the air does not affect the human body, is necessary.

In methods for sterilizing raw water using conventional electrolytic cells, there have been no satisfactory methods of sterilization, since the conventional electrolytic cells are also plagued by the aforementioned problems 1) through 3).

As a result of painstaking research on a method for manufacturing a novel bactericide by electrolysis, in light of the foregoing conventional techniques, the inventors completed the present invention upon discovering that by introducing raw water containing hydrochloric acid into an electrolytic cell without a diaphragm between the cathode and anode, and electrolyzing the raw water containing the hydrochloric acid, the bactericidal action of the resulting electrolytically treated liquid could be dramatically improved, and this electrolytically treated liquid could be used as a bactericide having excellent bactericidal action.

SUMMARY OF THE INVENTION

Subsequent to the completion of the invention described in WO 97/17298, the present inventors engaged in research to develop a method for manufacturing a bactericide capable of being prepared at a further higher electric power efficiency and a method for manufacturing a bactericide containing no ozone but containing chlorine alone, and have found that chlorine alone can be generated without the generation of ozone by changing the structure of the electrodes in an electrolytic cell to raise electric power efficiency and employing such an electrolytic cell to electrolyze hydrochloric acid in a specific range of voltage.

The present invention relates to a method for manufacturing a novel bactericide comprising an electrolytically treated liquid having high bactericidal action prepared from raw water by using electrolysis, wherein less electric power and water are required, the structure of the apparatus used therefore is a small scale, simple, and can be operated for long periods of time, and can reduce the manufacturing costs, and further relates to the apparatus for manufacturing the same, the bactericide that is manufactured by such a method, and a sterilizing method.

The present invention relates to a method for manufacturing a bactericide comprising an electrolytically treated liquid having high bactericidal action, comprising introducing raw water containing hydrochloric acid into an electrolytic cell without a diaphragm between the cathode and anode, applying electric current between the cathode and anode immersed in the raw water containing the hydrochloric acid to electrolyze the raw water containing the hydrochloric acid, and then recovering the liquid thus electrolytically treated, and further relates to an apparatus for manufacturing the same, the bactericide that is manufactured by this method, and a method for sterilizing raw water.

The present invention also relates to a method for manufacturing a bactericide capable of being prepared at a higher electric power efficiency as compared to that disclosed in WO 97/17298, and a method for manufacturing a bactericide containing no ozone but containing chlorine alone.

Moreover, the present invention relates to a method for sterilizing and treating raw water capable of being performed at a higher electric power efficiency as compared with that disclosed in WO 97/17298, without the generation of ozone.

An object of the present invention is to provide a method for manufacturing a novel bactericide, in which the aforementioned drawbacks of the conventional technology are remedied, and in which there is no need for discarding alkali ion water, that is, in which all of the starting raw water containing hydrochloric acid is obtained in the form of a bactericide having high bactericidal action, and to provide a method for manufacturing a novel bactericide, in which there is no need for a diaphragm in the electrolytic cell, in which the structure of the apparatus is simple, and in which large amounts of a bactericide can be obtained with a small-scale apparatus, and to provide a manufacturing method in which the apparatus can be operated for long periods of time without any concern over scaling, and in which a bactericide having high bactericidal effects can be produced easily and inexpensively.

Another object of the present invention is to provide an apparatus for the easy production of the aforementioned bactericide having high bactericidal effects.

Yet another object of the present invention is to provide a bactericide comprising an electrolytically treated liquid having high bactericidal action which is produced by the aforementioned method.

Still another object of the present invention is to provide a method for sterilizing raw water using the aforementioned method.

It is another object of the present invention to provide a method for manufacturing a bactericide capable of being prepared at a higher electric power efficiency as compared with that disclosed in WO 97/17298, and containing no ozone but containing chlorine alone.

It is still another object of the present invention to provide a method for sterilizing and treating raw water capable of being performed at a higher electric power efficiency as compared with that disclosed in WO 97/17298, without the generation of ozone.

The first of the inventions for resolving the aforementioned drawbacks is a method for manufacturing a bactericide comprising an electrolytically treated liquid having high bactericidal action, comprising introducing raw water containing hydrochloric acid into an electrolytic cell having no diaphragm between the cathode and anode, applying electric current between the cathode and anode immersed in the raw water containing the hydrochloric acid to electrolyze the raw water containing the hydrochloric acid, and then recovering the liquid thus electrolytically treated.

DESCRIPTION OF THE PREFERRED EMBODIMENTS

In a preferred embodiment, the processes of the introduction of the raw water containing hydrochloric acid, the electrolytic treatment, and the recovery of the electrolytically treated liquid are carried out continuously, and in which the raw water containing the hydrochloric acid is prepared by diluting hydrochloric acid of a hydrochloric acid molar concentration of between 0.001 mol/L and 6.4 mol/L, in which the electrolytically treated liquid is recovered after being diluted with water, in which the electrolytically treated liquid is recovered at an available chlorine concentration of at least 0.1 ppm, in which the electric current is applied in the form of alternating current with a frequency of more than 0 Hz and no more than 5 Hz, in which the electric current is applied at an electrical quantity rate of between 0.4 and 6.0 Coulombs per milliliter raw water containing hydrochloric acid, and in which the raw water containing hydrochloric acid has a pH between. 0.5 and 3.0.

The second of the inventions for resolving the aforementioned drawbacks is the bactericide that is produced by the first invention.

The third of the inventions for resolving the aforementioned drawbacks is a method for sterilizing raw water, characterized in preparing raw water containing hydrochloric acid by adding hydrochloric acid to raw water, recovering an electrolytically treated liquid by implementing the method of the first invention, and then obtaining the electrolytically treated liquid thus recovered in the form of sterilized raw water. In a preferred embodiment of the third invention, the preferable processes that can be adopted comprise adding hydrochloric acid to a part of raw water to prepare raw water containing hydrochloric acid, recovering an electrolytically treated liquid by implementing the method of the first invention, and returning the electrolytically treated liquid thus recovered to the raw water.

The fourth of the inventions for resolving the aforementioned drawbacks is an apparatus for manufacturing a bactericide comprising an electrolytically treated liquid having high bactericidal action, comprising an electrolytic cell in which the cathode and anode are arranged without being separated by a diaphragm, a water transport means for introducing raw water into the electrolytic cell, a hydrochloric acid adding means for adding hydrochloric acid to the raw water that is introduced through the water transport means, and discharge piping for discharging the electrolytically treated liquid from the electrolytic cell. A preferable embodiment that can be adopted is that an apparatus for manufacturing a bactericide comprising an electrolytically treated liquid having high bactericidal action, comprising an electrolytic cell in which the cathode and anode are arranged without being separated by a diaphragm, a hydrochloric acid-containing raw water reservoir means for storing raw water containing hydrochloric acid, a hydrochloric acid containing raw water transport means for introducing raw water containing hydrochloric acid from the hydrochloric acid-containing raw water reservoir means into the electrolytic cell, and discharge piping for discharging the electrolytically treated liquid from the electrolytic cell. In a preferred embodiment, the discharge piping may be equipped with an electrolytically treated liquid dilution means in which water is mixed with the electrolytically treated liquid to dilute it.

A preferred embodiment of the method for manufacturing a bactericide according to the first invention of the present inventions is that no diaphragm is provided between the cathode and the anode of the electrolytic cell, and that at least one unwired electrode, which is neither a cathode nor an anode, is provided, namely, that the electrolytic cell is an electrolytic cell connected in series.

A preferred embodiment of the method for manufacturing a bactericide according to the first invention of the present inventions is that the voltage between neighboring pair electrodes is more than 1.3 volts and less than 3.9 volts in applying an electric current.

A preferred embodiment of the above method for sterilizing and treating raw water according to the third invention of the present inventions is that the electrolytic cell is an electrolytic cell connected in series, and that the voltage between neighboring pair electrodes is more than 1.3 volts and less than 3.9 volts in applying an electric current.

The present invention is described in detail below, beginning with the method for manufacturing a bactericide, which is the first of the present inventions.

In the first of the present inventions, raw water containing hydrochloric acid is defined as water containing hydrochloric acid, or an aqueous solution containing hydrochloric acid added in which a chemical substance has been dissolved, but the use of raw water containing hydrochloric acid obtained by adding a relatively high concentration of hydrochloric acid to water is preferable to exhibit the effects of the present invention. In other words, the use of hydrochloric acid-containing raw water containing only hydrogen chloride is preferred. In this case, too high a concentration of hydrochloric acid results in an irritating odor due to the production of hydrogen chloride gas, which can sometimes corrode surrounding materials, so the concentration of the hydrochloric acid should not be too high when the present invention is implemented. In fact, the prescribed amount of hydrochloric acid as standardized food additive (36.46%, by Junsei Kagaku) was placed in 500 cc beaker and gradually diluted with the prescribed amount of pure water to check for the presence or absence of irritating odor. Irritating odor was detected at hydrochloric acid molar concentrations of 9.5 mol/L, 7.7 mol/L, and 7.0 mol/L, whereas detection fell off at a concentration of 6.4 mol/L, with none at concentrations lower than 6.0 mol/L. In the present invention, therefore, the hydrochloric acid molar concentration should be no more than 6.4 mol/L in the preparation of the raw water containing hydrochloric acid. As will be described below, moreover, the hydrochloric acid molar concentration of the raw water containing hydrochloric acid after preparation with hydrochloric acid should be at least 0.001 mol/L, so the molar concentration of the starting material hydrochloric acid should naturally be at least 0.001 mol/L. That is, 0.001 mol/L hydrochloric acid should be used in the raw water containing hydrochloric acid without being diluted.

The raw water containing hydrochloric acid is introduced by a raw water pump from a raw water tank through a raw water supply pipe to an electrolytic cell having no diaphragm. The prescribed amount of hydrochloric acid from the hydrochloric acid tank is mixed by the hydrochloric acid pump in the raw water supply pipe, the pH of the raw water is adjusted to between 0.5 and 3.0, and preferably between 0.8 and 3.0, and the resulting raw water thus containing hydrochloric acid is introduced into the electrolytic cell having no diaphragm. Previously prepared raw water containing hydrochloric acid may be introduced without modification. A means for introducing the liquid can also be selected as desired.

A cathode and anode are arranged in the electrolytic cell without being separated by a diaphragm. The raw water containing hydrochloric acid is electrolytically treated by immersing the cathode and anode in the raw water, and applying electric current between them to electrolyze the raw water containing hydrochloric acid. Either alternating or direct current with a frequency of more than 0 Hz and no more than 5 Hz, and preferably more than 0 Hz and no more than 2 Hz, is applied at a rate of 0.4 to 6.0 Coulombs, and preferably 0.8 to 3.0 Coulombs, per milliliter raw water containing hydrochloric acid.

The electrolytically treated liquid is removed from the electrolytic cell through the electrolytically treated liquid discharge pipe, and can be used as a bactericide without further modification or after being diluted with water.

As noted in the conventional techniques described above, electrolytic cells used to electrolyze ordinary water have a structure in which the anode and cathode are separated by a diaphragm. In general, being not limited to the electrolysis of water, electrolytic treatments are often carried out to separate various products from a solution, and electrolytic cells with diaphragms are commonly used for that purpose. However, in the present invention, since the electrolytic treatment is carried out to convert the properties of the raw water containing hydrochloric acid, there is no need to separate the liquid produced by the anode and the liquid produced by the cathode, making it possible to use an electrolytic cell having no diaphragm.

Electrolytic treatment of raw water containing hydrochloric acid in an electrolytic cell having no diaphragm is assumed to dramatically improve the bactericidal effects of the electrolytically treated water for the following reasons.

During the electrolytic treatment, chlorine ions are oxidized on the surface of the anode and are converted into hypochlorous acid. As a result, a liquid having high bactericidal action is produced.

Hydrogen gas is produced on the surface of the cathode, meanwhile, resulting in a higher pH, but since there is no diaphragm between the anode and cathode chambers in the electrolytic cell used in the manufacturing method of the present invention, the two types of water become mixed, and the pH increases somewhat because part of the hydrochloric acid is converted to hypochlorous acid, but it is assumed that, as a result, the bactericidal action produced by the anode remains unaffected in the electrolytically treated liquid, and all of the raw water containing hydrochloric acid is converted to an electrolytically treated liquid having high bactericidal action.

A preferred embodiment of the first of the present inventions is described below.

The electrolytic treatment can be carried out continuously in the manufacturing method pertaining to the present invention. That is, the raw water containing hydrochloric acid is continuously introduced to the electrolytic cell, where it undergoes continuous electrolytic treatment, and the electrolytically treated liquid is continuously taken out. This allows large amounts of a bactericide to be manufactured.

In the manufacturing method pertaining to the present invention, the electrolytically treated liquid may be recovered after being diluted with water. That is, after the raw water of low pH containing hydrochloric acid has been electrolytically treated, the electrolytically treated liquid can be diluted with water to obtain a bactericide of the desired concentration. In general, when the raw water containing hydrochloric acid has a low pH, the electrical resistance is lowered during the electrolytic treatment, and the electrolytic treatment can be carried out at a lower voltage, allowing lower amounts of electric power to be used. Furthermore, when the raw water of low pH containing hydrochloric acid is electrolytically treated in just low amounts and is then diluted, the amount of liquid that is electrolytically treated is low, allowing large amounts of bactericide to be obtained with small-scale equipment.

In this case, as will be described in the test examples below, the bactericidal effects are reduced when the available chlorine concentration of the diluted electrolytically treated liquid is diluted to less than 0.1 ppm. It is thus preferable in terms of bactericidal effects to limit the dilution of the electrolytically treated liquid to an available chlorine concentration of at least 0.1 ppm following dilution. The available chlorine concentration of an electrolytically treated liquid is generally affected by the current level when electricity is applied, but in any case the available chlorine concentration of the bactericide should be at least 0.1 ppm.

Considered in terms of pH, the diluted electrolytically treated liquid should have a pH of no more than 7.0, and preferably between 3.5 and 6.5. That is because the free hypochlorous acid in the liquid is relatively stable when the pH of the diluted electrolytically treated liquid is within this range.

Direct current can be applied in the same manner as in the past during the electrolytic treatment in the manufacturing method pertaining to the present invention. However, in this case, the electrolytic cell of the present invention has the advantage of less scale on the cathode surface than in conventional electrolytic cells. Because of the absence of a diaphragm in the electrolytic cell of the present invention, the anode water and cathode water become mixed, and the raw water containing hydrochloric acid also has a low pH, thereby avoiding increases in pH at the cathode surface.

However, the use of alternating current is preferred during the electrolytic treatment in the manufacturing method pertaining to the present invention. That is because, even though the cathode and anode can be suitably reversed due to the absence of a diaphragm in the electrolytic cell used in the manufacturing method pertaining to the present invention, the cathode and anode can be reversed at fixed periods when alternating current is applied, thereby allowing scale on the cathode surface to be controlled more effectively than when direct current is used.

Alternating current is preferred because, although the waveform of the current is not particularly limited when current is supplied to periodically reverse the cathode and anode, the cathode and anode can be reversed instantly when the waveform is rectangular, as will be described in the embodiments below.

In the manufacturing method pertaining to the present invention, the frequency of the alternating current that is applied should be more than 0 Hz and no more than 5 Hz. That is because there is no reaction during the electrolytic treatment when the alternating current has a frequency that is too high. As will be described in the test examples below, the use of alternating current of no more than 5 Hz, and preferably no more than 2 Hz, is preferred. The expression "a frequency of more than 0 Hz" does not include 0 Hz; alternating current with a frequency of 0 Hz means direct current.

In the manufacturing method pertaining to the present invention, the electrolytic treatment is carried out at an electrical quantity rate of between 0.4 and 6.0 Coulombs per milliliter raw water containing hydrochloric acid (hereinafter, units of Coulombs per milliliter of raw water containing hydrochloric acid are sometimes given as c/mL).

As will be described below in the test examples, when the electrolytic treatment is carried out in an electrical quantity of at least 0.4 Coulombs per milliliter raw water containing hydrochloric acid, the bactericide has better bactericidal effects, while 0.8 Coulombs or more is preferred because even more potent bactericidal effects are obtained.

When the electrical quantity is more than 6.0 c/mL, the effects of the electrolytic treatment are higher than necessary, resulting in more wasted power. That is, greater amounts of gases such as chlorine gas, hydrogen gas, and oxygen gas are produced, but there is no proportionate increase in the inherent bactericidal effects of the electrolytically treated liquid, resulting in more wasteful consumption of power. The electrical quantity should accordingly be no more than 6.0 c/mL.

The raw water containing hydrochloric acid that is used in the manufacturing method pertaining to the present invention has a pH of between 0.5 and 3.0. When the raw water containing hydrochloric acid has a pH of no more than 3.0, an advantage is that the electrical resistance is lowered during the electrolytic treatment, and the electrolytic treatment can be carried out at a lower voltage. However, when the pH is extremely low, there is no proportional increase in the bactericidal effects of the electrolytically treated liquid with the increase in the amounts of gases such as chlorine, hydrogen, and oxygen that are produced during electrolytic treatment, resulting in a greater waste of power. The pH of the raw water containing the hydrochloric acid should accordingly be at least 0.5, and preferably at least 0.8. The pH of the raw water containing hydrochloric acid is important because it affects efficiency and the like during the electrolytic treatment.

Viewed in terms of the concentration of the raw water containing hydrochloric acid, the hydrochloric acid molar concentration of the raw water containing hydrochloric acid should be between 0.001 mol/L and 1 mol/L.

When the method pertaining to the present invention is performed in the home, at work, in a restaurant, or the like, the use of previously prepared raw water containing hydrochloric acid is preferred because it is difficult to prepare hydrochloric acid-containing raw water from high concentration hydrochloric acid. In this case, the hydrochloric acid molar concentration of the raw water containing hydrochloric acid is preferably between 0.05 and 0.2 mol/L, because little power is wasted within the range where the bactericidal effects can be maintained, and there is little scale on the cathode surface even when direct current is used.

The second of the inventions is a bactericide produced by the manufacturing method described above. Because raw water containing hydrochloric acid is used as the starting material, the bactericide pertaining to the present invention is devoid of foul odor or disagreeable taste other than an acidic taste, and characteristically leaves no residue after drying. It is thus particularly suitable for use in the fields of the food industry, medical products industry, and the like when piping, packing devices, containers, and the like are to be sterilized. The bactericide pertaining to the present invention which is manufactured by the manufacturing method described above is preferably diluted with water, and is adjusted so that the pH following dilution is no more than 7.0, and is preferably between 3.5 and 6.5.

The third of the inventions is a method for sterilizing raw water using the method of the first invention.

The first of the inventions can be used as a method for sterilizing raw water. In the present invention, raw water means, specifically, water or an aqueous solution in which a chemical substance has been dissolved, such as an aqueous solution or suspension with a total solids concentration of no more than 300 ppm, but it can also mean a liquid which should or must be sterilized.

When hydrochloric acid is added to such raw water to prepare raw water containing hydrochloric acid, and the raw water is electrolyzed by the electrolytic treatment of the first of the inventions, the resulting electrolytically treated liquid can be regarded as sterilized raw water. In an embodiment, hydrochloric acid may also be added to a part of raw water so as to prepare raw water containing hydrochloric acid, being followed by the electrolytic treatment of the first of the inventions similarly to recover the electrolytically treated liquid, and the electrolytically treated liquid thus recovered may be returned to the raw water.

In the method in the third of the inventions, no alkaline water is produced as in conventional techniques, so there is no need to discard any alkaline water. The third invention can be used to carry out a sterilization treatment without discarding any raw water. That is, it can be considered a method of sterilization that resolves problems 1) through 3) caused by conventional electrolytic cells.

Because, as described above, a sterilization treatment can be performed without discarding alkaline water in the third of the inventions, it has an extremely broad range of applications and can be used to sterilize a variety of liquids. Examples of raw water in the third of the inventions include, but, or course, are not limited to, drinking water, various types of wastewater, cooling tower cooling water, water serving as starting material for ice, toilet flushing water, and stored water for baths, pools, water tanks, fishing ponds, and the like. A specific embodiment of the third of the inventions is described below.

A preferred embodiment of the first to third inventions of the present inventions is that the electrolytic cell is an electrolytic cell connected in series.

Generally, as methods for connecting a plurality of electrodes in the electrolytic cell can be mentioned two kinds, connecting in parallel and connecting in series. A method for connecting in parallel is a method for connecting all electrodes to the cathode or the anode of an electric source, and a method for connecting in series is a method in which, for example, a plurality of electrodes are piled at a certain distance to form a structure of interactive insulation and there exists at least one unwired electrode connected to neither of the cathode and the anode between the electrode connected to the anode of an electric source (namely, anode) and the electrode connected to the cathode of the electric source (namely, cathode).

Generally, in the preparation of electrolytic water, it is preferable from the viewpoint of economics to generate as much chlorine as possible in the process of electrolysis to prepare a small amount of water with a high chlorine concentration and then to dilute this properly to use as a bactericide. In the case of preparing a small amount of water with a high chlorine concentration, the electrolytic cell can be miniaturized, which is advantageous from the viewpoints of equipment investment, manufacturing costs and energy efficiency. For this purpose, it is preferable to employ raw water containing hydrochloric acid with a chlorine concentration as high as possible to obtain a bactericide with a high effective chlorine concentration.

Raw water containing hydrochloric acid with a high chlorine concentration has a high electric conductivity; in the case of employing the electrolytic cell connected in series for electrolyzing raw water containing hydrochloric acid with such a high electric conductivity, the following advantages have been reported:

1) In the Case of Employing an Electric Source with a Certain Voltage

In the case that electrolysis is performed under the condition of a certain voltage, the value of an electric current rises as the electric conductivity of raw water containing hydrochloric acid becomes higher, and the life of electrodes is shortened by the rise of the value of an electric current. In the case of employing the electrolytic cell connected in series, however, the resistance value increases and thereby the rise of the value of an electric current can be checked. Hence, a problem of shortening the life of electrodes does not occur.

2) In the Case of Employing an Electric Source with a Certain Electric Current

In the case that electrolysis is performed under the condition of a certain electric current, voltage drops as the electric conductivity of raw water containing hydrochloric acid becomes higher, and it may become difficult to secure electrolytic voltage needed. In the case of employing the electrolytic cell connected in series, however, the resistance value can be varied, and thereby the drop of voltage can be avoided. Hence, it is possible to operate under optimum conditions.

3) In the Case of Performing Electrolysis under the Conditions with neither a Certain Voltage nor a Certain Electric current As the chlorine ion concentration of raw water containing hydrochloric acid rises, the value of an electric current and/or the value of voltage vary; in the case of employing the electrolytic cell connected in series, however, the value of an electric current or the value of voltage can be returned to the same one by adding an unwired electrode according to the rise of the chlorine ion concentration. Thereby, it is possible to operate without changing operation conditions.

However, the electrolytic cell connected in series has been employed in the case of preparing chlorine or caustic soda on an industrial scale ("Soda and Chlorine", Vol. 26, No. 4, p. 112, 1975), but it has never been employed in the process of manufacturing a bactericide.

The reason is that the following has been known: generally, in the case of employing the electrolytic cell connected in series, as the number of unwired electrodes increases, the amount of chlorine generated increases advantageously; however, the amount of chlorine generated per unit electric power decreases and electric power efficiency decreases; thus, finally running costs increase.

Moreover, generally, the electrolytic cell connected in series is equal to electrodes connected in parallel which are connected in series, and hence voltage to be applied tends to become high though the volume of an electric current is small (Incorporated Association Japan Chemistry Society, "Kagaku Binran (Guide to Chemistry)", p. 99, Maruzen, 1965). In manufacturing a bactericide, the saline concentration of raw water is extremely thin as compared with other technical fields, and hence such a voltage rise is extremely large. Accordingly, since electric power consumption becomes large, electric power efficiency decreases sharply. It has been thought according to these reasons that, generally in the technical field of a bactericide, it is difficult to allow the electrolytic cell connected in series to come into practical use.

Finally, though the electrolytic cell connected in series have a lot of advantages, it has not been employed in the technical field of a bactericide since it cannot solve the problems of the rise of running costs and the excessive rise of voltage. Even if it is employed, it must be operated preparing for the rise of running costs.

However, the present invention introduces hydrochloric acid-containing raw water substantially containing no sodium chloride into the electrolytic cell. That is, since it employs hydrochloric acid-containing raw water substantially containing no sodium chloride, the electric power efficiency does not decrease, the running costs do not rise and the voltage does not rise excessively in spite of employing the electrolytic cell connected in series.

Conventionally, there has existed a problem of the excessive rise of voltage in the case of employing the electrolytic cell connected in series, which is caused by the reason that hydrochloric acid-containing raw water contains sodium chloride; in the case of employing hydrochloric acid-containing raw water substantially containing no sodium chloride as in the present invention, however, the voltage does not rise excessively in spite of employing the electrolytic cell connected in series. This is the fact found out by the present inventors for the first time.

As described above, the present invention can perform the preparation of an economical bactericide while making the most of the advantages of the electrolytic cell connected in series.

A preferred embodiment of the first to third inventions of the present inventions is that the voltage between neighboring pair electrodes is more than 1.3 volts and less than 3.9 volts in electrolysis. There exists an unwired electrode between the cathode and the anode in the case of the electrolytic cell connected in series, as described above; "voltage between neighboring pair electrodes" is a term meaning the voltage between neighboring pair electrodes including the cathode, the anode and the unwired electrode.

As will be described in Test Examples later, as the voltage is raised,. Chlorine begins to occur at a voltage of more than 1.3 volts, and the amount attains the maximum at a voltage of more than 1.5 volts.

Moreover, when the voltage exceeds 3.9 volts, oxygen begins to occur, and when it exceeds 5.0 volts, ozone begins to occur. Since the occurrence of ozone is undesirable and the occurrence of oxygen is wasteful for electric power efficiency, a voltage of less than 3.9 volts is preferable. Since the electric power efficiency reduces as the voltage becomes higher, a voltage of less than 3.0 volts is particularly preferable.

The fourth of the inventions is an apparatus for manufacturing the aforementioned bactericide, comprising at least an electrolytic cell in which the cathode and anode are arranged without being separated by a diaphragm, a water transport means for introducing raw water into the electrolytic cell, a hydrochloric acid adding means for adding hydrochloric acid to the raw water that is introduced through the water transport means, and discharge piping for discharging the electrolytically treated liquid from the electrolytic cell.

The electrolytic cell pertaining to the present invention is equipped with a container, cathode, and anode, and has no membrane separating the cathode and anode. The container constituting the electrolytic cell has an inlet for the raw water containing hydrochloric acid and an outlet for discharging the electrolytically treated liquid. The container may be any shape such as a rectangular column shape, cylindrical shape, or the like, and the container material should have excellent corrosion resistance against hydrochloric acid, such as polyvinyl chloride, FRP, and polyethylene. The electrodes may have a well-known shape, but the electrode material must be chemically stable when reacting with the raw water containing hydrochloric acid. Platinum is an ideal material. Discharge piping for discharging the electrolytically treated liquid is connected to the outlet for discharging the electrolytically treated liquid in the electrolytic cell.

The apparatus pertaining to the present invention has a structure in which the raw water is introduced into the electrolytic cell as relatively high concentration hydrochloric acid is diluted with raw water to prepare suitable raw water containing hydrochloric acid.

The raw water is introduced into the electrolytic cell by the water transport means. Although any water transport means may be used, examples of embodiments include those in which a raw water transport pipe branching from a tap water pipe or tap water faucet is connected via a water pump to the inlet of the electrolytic cell for the raw water containing hydrochloric acid. This scenario involves low equipment costs since it is a simple structure in which tap water is merely taken in directly from a tap water pipe. In an embodiment, as in the preferred embodiment described below, a raw water tank is located upstream of a water supply tank, and the raw water is introduced into the electrolytic cell after being temporarily stored in the raw water tank.

The apparatus pertaining to the present invention is equipped with a hydrochloric acid adding means for adding hydrochloric acid to the raw water that is introduced through the water transport means, that is, the raw water before it reaches the electrolytic cell. Any type of hydrochloric acid adding means may be used. As an example of one embodiment, when hydrochloric acid is commercially available in the form of filled containers, a hose may be directly inserted into the filled container, the other end of the hose may be connected to one end of a hydrochloric acid supply pipe, and the other end of the hydrochloric acid supply pipe may be connected to the raw water transport pipe.

As an example of an embodiment in which the hydrochloric acid supply pipe is connected to the raw water transport pipe, the end of the hydrochloric acid supply pipe may be fed into the raw water transport pipe, bent in the center of the raw water transport pipe in the direction in which the raw water flows, and then opened up. With this type of hydrochloric acid supply pipe, the hydrochloric acid is drawn into the interior of the raw water transport pipe by the pressure of the flow of the raw water, and the hydrochloric acid is automatically added to the flow of raw water by the ejector function. In this case, furthermore, the hydrochloric acid supply pipe is preferably provided with a regulating valve to adjust the amount that is added. The hydrochloric acid can also be forcibly introduced by a hydrochloric acid constant rate pump.

In addition to the aforementioned embodiment in which a hose is inserted into a container filled with hydrochloric acid, examples of hydrochloric acid adding means also include embodiments in which an outlet of a hydrochloric acid tank for storing hydrochloric acid is connected with the raw water transport pipe by means of the hydrochloric acid supply pipe via a hydrochloric acid constant rate pump. The part where the hydrochloric acid supply pipe and raw water supply pipe flow together may be located anywhere in the raw water transport pipe, and the hydrochloric acid constant rate pump is preferably a material with excellent corrosion resistance against hydrochloric acid. When the part where the hydrochloric acid supply pipe and raw water transport pipe flow together is upstream from the water pump, a material with excellent corrosion resistance against hydrochloric acid should also be used for the water pump. Examples of materials having excellent corrosion resistance against hydrochloric acid include Teflon (registered trademark), polyvinyl chloride, and polyethylene.

The operation of the apparatus pertaining to the present invention is described below. First, raw water is introduced by the water transport means into the electrolytic cell. Relatively high concentration hydrochloric acid is added by the hydrochloric acid adding means to the raw water before the raw water reaches the electrolytic cell. Raw water containing hydrochloric acid is thus introduced at an adjusted pH to the electrolytic cell. In the electrolytic cell, electric current is applied between the cathode and anode immersed in the raw water containing hydrochloric acid to effect the electrolytic treatment. The electrolytically treated liquid is discharged from the discharge piping set up in the electrolytic cell and can thus be obtained as a bactericide.

In another embodiment of the apparatus pertaining to the present invention, the structure is simpler, comprising a means for storing raw water containing hydrochloric acid and a means for introducing raw water containing hydrochloric acid instead of the aforementioned water transport means and hydrochloric acid adding means. The means for storing raw water containing hydrochloric acid is a means in which previously prepared raw water containing hydrochloric acid is temporarily stored. Although a simple container can be used, the material is preferably not corroded by hydrochloric acid. The means for introducing raw water containing hydrochloric acid is a means in which the raw water containing hydrochloric acid is introduced from the means for storing the raw water containing hydrochloric acid into the electrolytic cell. Examples of this device include pumps and ejectors.

A simple container may be used for the means for storing the raw water containing hydrochloric acid, examples of which include structures similar to the structure of the aforementioned hydrochloric acid adding means, such as embodiments in which a hose is directly inserted into the container, and the other end of the hose is connected to the electrolytic cell.

In this type of embodiment, previously prepared raw water containing hydrochloric acid is introduced by the means for storing raw water containing hydrochloric acid and the means for introducing the raw water containing hydrochloric acid into the electrolytic cell, allowing a bactericide to be obtained.

In the apparatus pertaining to the present invention, the discharge piping is equipped with an electrolytically treated liquid-diluting means in which water is mixed with the electrolytically treated liquid to dilute it. The means for diluting the electrolytically treated liquid may be any that allows water to be added to the electrolytically treated liquid discharged from the electrolytic cell, examples of which include embodiments in which the electrolytically treated liquid is temporarily stored in an open tank, and water is added to and mixed in this tank at a flow rate according to the flow rate and pH of the electrolytically treated liquid. To maximize the bactericidal effects of the resulting bactericide, the electrolytically treated liquid discharged from the electrolytic cell should be diluted with water as soon as possible. Because the electrolytically treated liquid contains a variety of gases, it should be diluted in an air-tight state.

The apparatus pertaining to the present invention can also be used as an apparatus for sterilizing raw water. When the apparatus pertaining to the present invention is used as such an apparatus for sterilizing raw water, discharge piping may be connected to piping or the like through which the raw water flows, and the electrolytically treated liquid may be mixed and diluted with raw water. When the aforementioned discharge piping is equipped with a means for diluting the electrolytically treated liquid, the electrolytically treated liquid is diluted with "water," although the term "water" encompasses raw water.

An example of a preferred embodiment of the apparatus pertaining to the present invention is depicted in FIG. 1.

The apparatus depicted in FIG. 1 is an example of an embodiment of the apparatus pertaining to the present invention. FIG. 1 is a diagram depicting an embodiment of the apparatus pertaining to the present invention.

In FIG. 1, a raw water supply pipe 1a is connected to a raw water tank 1. Because the raw water W is supplied through a float valve (not shown in figure), the water level of the raw water tank 1 is kept constant. A raw water transport pipe 2 connects the raw water tank 1 via a raw water pump 3 to an electrolytic cell 5. In addition, a hydrochloric acid supply pipe 10 leading from a hydrochloric acid tank 9 and joining the raw water supply pipe 2 via a hydrochloric acid constant rate pump 4 is connected to the raw water supply pipe 2 at a location 10a upstream from the raw water pump 3. An electrolytically treated liquid discharge pipe 8 through which the bactericide is discharged is connected to the electrolytic cell 5. The electrolytic cell 5 is a single chamber in which there is no diaphragm separating the cathode and anode, and the electrodes 7 are arranged so that each is connected to a power source 6.

The operation of the apparatus having the aforementioned structure is described below. The raw water W is introduced by the raw water pump 3 through the raw water supply pipe 2 into the electrolytic cell 5. Relatively high concentration hydrochloric acid A is injected by the hydrochloric acid constant rate pump 4 through the hydrochloric acid supply pipe 10 into the raw water W. The raw water W which has thus been introduced into the electrolytic cell is now hydrochloric acid-containing raw water AW of a constant concentration. An electrolytic treatment is then performed by applying electricity to the electrodes 7 in the electrolytic cell 5, but since the reduced liquid at the cathode and the oxidized liquid at the anode are always mixed in the electrolytic cell, the pH is virtually the same as the hydrochloric acid containing raw water AW prior to the electrolytic treatment. The chlorine, hypochlorous acid, ozone, and the like produced by the oxidation reaction at the anode strongly tend to exist in a relatively stable free state because of the pronounced acidity of the electrolytically treated liquid and the like. The hydrochloric acid-containing raw water AW accordingly results in an electrolytically treated liquid with pronounced oxidation action, and an electrolytically treated liquid E that can be used as a bactericide of low pH, considerable oxidation action, and high bactericidal action is discharged from the electrolytically treated liquid discharge pipe 8.

The apparatus depicted in FIG. 2 is an example of another embodiment of the apparatus pertaining to the present invention. FIG. 2 is a diagram depicting another embodiment of the apparatus pertaining to the present invention. In the apparatus in FIG. 2, the main components of the structural elements are the same as those of the apparatus depicted in FIG. 1, as indicated by the use of the same symbols as those in FIG. 1, and these will not be discussed in any further detail.

The apparatus in FIG. 2 is equipped with a means for diluting the electrolytically treated liquid. The raw water tank 1 is equipped with a diluting water transport pipe 12, separately from the raw water transport pipe 2, as a means for diluting the electrolytically treated liquid. At a junction point 12a, the diluting water transport pipe 12 joins the electrolytically treated liquid discharge pipe 8 leading away from the electrolytic cell 5. A bactericide transport pump 11 is set up downstream of the junction point 12a. A flow rate regulating valve 13 is also set up in the diluting water transport pipe 12. The other structural elements are the same as those of the apparatus in FIG. 1.

The operation of the apparatus in FIG. 2 is described below. The electrolytically treated liquid E discharged from the electrolytic cell 5 flows through the electrolytically treated liquid discharge pipe 8 and joins, at junction point 12a, the diluting water being transported through the diluting water transport pipe 12, with which it is mixed and diluted. The diluted electrolytically treated liquid is transported by the bactericide transport pump 11, and can be recovered in the form of a bactericide Ed. The diluting water flow rate can be regulated by the flow rate regulating valve 13.

In the embodiment in FIG. 2, the electrolytically treated liquid E discharged from the electrolytic cell 5 can be directly diluted, so a characteristic effect is that the gases contained in the electrolytically treated liquid E are not removed.

The apparatus depicted in FIG. 3 is an example of another embodiment of the apparatus pertaining to the present invention. FIG. 3 is a diagram depicting another embodiment of the apparatus pertaining to the present invention. In the apparatus in FIG. 3, the main components of the structural elements are the same as those of the apparatus depicted in FIG. 1, as indicated by the use of the same symbols as those in FIG. 1, and these will not be discussed in any further detail.

The apparatus in FIG. 3 is equipped with a means 14 for storing the raw water containing hydrochloric acid, and this means 14 for storing raw water containing hydrochloric acid is connected to the electrolytic cell 5 by means of a hydrochloric acid-containing raw water pipe 15. The electrolytically treated liquid discharge pipe 8 for discharging the bactericide is connected to the electrolytic cell 5, but the electrolytically treated liquid discharge pipe 8 is also connected by way of an orifice 16 to an ejector 19, and the diluting water transport pipe 12 is also connected to the ejector 19. The diluting water transport pipe 12 is equipped with a constant flow rate valve 18 and is connected to a diluting water source 17. The other structural elements are the same as those in the apparatus in FIG. 1.

The operation of the apparatus in FIG. 3 is described below. Previously prepared hydrochloric acid-containing raw water AW is stored in the means 14 for storing raw water containing hydrochloric acid. The diluting water flows from the diluting water source 17 through the diluting water transport pipe 12 into the ejector 19 (in the direction indicated by arrow Y), and the flow rate is controlled in a stable manner by the constant flow rate valve 18. Because the ejector 19 suctions the electrolytically treated liquid discharge pipe 8, the hydrochloric acid-containing raw water AW stored in the means 14 for storing the hydrochloric acid-containing raw water flows through the hydrochloric acid-containing raw water pipe 15 (in the direction indicated by arrow X1) and is introduced into the electrolytic cell 5. The electrolytically treated Liquid E discharged from the electrolytic cell 5 flows through the electrolytically treated liquid discharge pipe 8 to the ejector (in the direction indicated by arrow X2) and is diluted by the diluting water from the diluting water source 17. The diluted electrolytically treated liquid can be recovered as the bactericide Ed. The ratio of the flow rate of the electrolytically treated liquid to the flow rate of the diluting water is adjusted by the orifice 16 previously set up in the electrolytically treated liquid discharge pipe 8.

In the apparatus in FIG. 3, the ejector 19 doubles as a means for introducing the water containing the hydrochloric acid, resulting in a simpler structure.

An embodiment featuring the use of the apparatus in FIG. 3 is described below. A bactericide manufactured by means of the apparatus in FIG. 3 can be added, for example, to the water that is used to flush toilets. Flush toilets are in general readily contaminated by germs, and there are often germ-related stains. The use of an electrolytic cell in such cases is well known, but since the aforementioned problems 1) through 3) occur in conventional electrolytic cells, a more desirable flush toilet can be made using the apparatus in FIG. 3.

FIG. 4 is a diagram depicting a flush toilet featuring the use of the apparatus in FIG. 3. In FIG. 4, structural elements which are the same as those in FIG. 3 are indicated by the same symbols as those in FIG. 3, and will not be discussed in any further detail.

In FIG. 4, a flushing water transport pipe 24 is connected to a toilet 25, and the flushing water transport 24 is connected to a cistern 23. Flushing water is stored in the cistern 23.

The cistern 23 is equipped with a float valve 21, a flushing water transport pipe 12a is connected to the float valve 21, and the end of the flushing water transport pipe 12a is connected to a flushing water supply source 17a. The flushing water transport pipe 12 is equipped with the apparatus 20 for manufacturing a bactericide as depicted in FIG. 3.

The operation of the apparatus in FIG. 4 is described below. When flushing water flows from the flushing water transport pipe 24 to the toilet 25, the water level of the cistern 23 drops. The position of the float 22 of the float valve 21 drops, and the float valve 21 opens, allowing flushing water WO to flow from the flushing water supply source 17a through the flushing water transport pipe 12a to the cistern 23. The flushing water WO is introduced until the water level of the cistern is restored.

At this time, the bactericide is manufactured by the operation of the bactericide manufacturing device 20, and the bactericide is introduced through the injector 19 and is mixed with the flushing water WO. As a result, sterilized flushing water flows into the cistern 23, flushing water transport pipe 24, and toilet 25. The operation of the bactericide manufacturing apparatus 20 can be automated in a variety of ways in conjunction with the float valve 21. A pump may also be used as an alternative to the aforementioned ejector 19.

The bactericide manufactured in the apparatus in FIG. 4 can be used effectively since it does not suffer from the aforementioned problems 1) through 3) typical of conventional electrolytic cells. The apparatus in FIG. 4 can be used to particular advantage in noncistern types of flush toilets.

Toilets with showers have recently become popular. In these types of flush toilets, which allow the anus to be rinsed with the shower following evacuation, it is extremely hygienic to use the bactericide manufactured by the apparatus of the present invention as the shower water. In this case, the shower operation should be automated in conjunction with the apparatus of the present invention.

An embodiment of the sterilization method in the third of the inventions is described below. For the convenience of description, a sterilizing apparatus is given as an example. The description of the apparatus is given in lieu of a description of the sterilization method.

The sterilizing method of the present invention can be implemented using the apparatus depicted in FIG. 5, for example. FIG. 5 is a diagram depicting an example of a sterilizing apparatus for implementing the sterilizing method of the present invention. The apparatus in FIG. 5 is a modification of some of the structural elements of the apparatus in FIGS. 1 through 3. Most of the structural elements are the same as those in the apparatus depicted in FIGS. 1 through 3, as indicated by symbols that are the same as those in FIGS. 1 through 3, and these will not be discussed in further detail.

In FIG. 5, one end of the raw water transport pipe 2 is connected to a raw water supply source 17b. The raw water transport pipe 2 is branched between raw water transport pipes 2a and 2b, and the raw water transport pipe 2b is equipped with a sterilizing apparatus 30. The sterilizing apparatus 30 is an adaptation of the apparatus depicted in FIG. 2. The raw water transport pipe 2a is equipped with a flow rate regulating valve 32, and the raw water transport pipe 2b is equipped with a flow rate regulating valve 31. The electrolytically treated liquid discharge pipe 8 joins the raw water transport pipe 2a, forming a raw water transport pipe 2c.

The operation of the apparatus in FIG. 5 is described below. Raw water W1 flows (in the direction indicated by the arrow Y) from the raw water supply source 17b by means of a pump not shown in the figure to the raw water transport pipe 2, where it is separated off to the raw water transport pipes 2a and 2b (in the directions indicated by the arrows Y1 and Y2, respectively). The flow rate ratio is adjusted by means of the flow rate regulating valves 31 and 32. Relatively high concentration hydrochloric acid A is injected through the hydrochloric acid supply pipe 10 to the raw water flowing through the raw water transport pipe 2b. This is then introduced into the electrolytic cell, where it is electrolytically treated, and is discharged (in the direction of the arrow X2) from the electrolytically treated liquid discharge pipe 8. The electrolytically treated liquid joins the raw water flowing through the raw water transport pipe 2a and flows through the raw water transport pipe 2c (in the direction indicated by the arrow Y3). The raw water W1 is thus sterilized.

In the apparatus in FIG. 5, there is no need to discard alkaline water since no alkaline water is produced as in conventional electrolytic cells. Part of the raw water W1 is collected by means of the raw water transport pipe 2b and is used to prepare the hydrochloric acid-containing raw water AW, so the flow rate of the raw water W1 following sterilization is not significantly increased.

Embodiments featuring the use of the apparatus in FIG. 5 are described below. The first example features the sterilization of water for drinking to make drinking water. In this case, the "raw water supply source 17b" in FIG. 5 is the supply source for water for drinking. That is, water for drinking that flows from the supply source 17b for water for drinking is sterilized by the apparatus in FIG. 5, resulting in water that is suitable for drinking, and is supplied as tap water or the like.

The sterilization of wastewater from factories, households, or the like is another example of an embodiment featuring the use of the apparatus in FIG. 5. In this case, the "raw water supply source 17b" in FIG. 5 is the wastewater discharge source. That is, environmental pollution caused by pathogens and the like can be prevented when the wastewater discharged from the wastewater discharge source 17b is sterilized by the apparatus in FIG. 5 and allowed to flow into rivers, underground, or the like.

In another embodiment featuring the use of the apparatus in FIG. 5, water that has been sterilized by the apparatus in FIG. 5 can be frozen to obtain sanitary ice. In general, when fresh seafood is transported, it is often packed in ice to preserve freshness, but the ice used for that purpose should be sanitary. When ice is made from water that has been sterilized by the apparatus in FIG. 5, the bactericidal action is preserved, making it sanitary.

Another embodiment featuring the use of the apparatus in FIG. 5 is described below. The sterilization of cooling tower water depicted in FIG. 6 can be given as an example. FIG. 6 is a diagram depicting an example of the sterilizing apparatus in FIG. 5 equipped with cooling water piping for a cooling tower. In FIG. 6, a cooling tower 33 and a condenser 34 for the refrigerating equipment are connected by circulation piping 37. The circulation piping 37 is provided with a pump 35.

The circulation piping 37 is provided with the sterilizing apparatus 30 shown in FIG. 5 above. The circulation piping 37 is also equipped with a chlorine concentration meter 36, and the output line 36a of the chlorine concentration meter is connected to a controller 38. The output line 4a of the controller 38 is connected to the hydrochloric acid constant rate pump 4 of the sterilizing apparatus 30, and the output line 6a is connected to a power source 6.

The operation of the apparatus in FIG. 6 is described below. Cooling water is circulated (in the direction indicated by the arrow Y) through the circulation piping 37 by the pump 35, and the chlorine concentration of the cooling water is measured by the chlorine concentration meter 36. The level of the chlorine concentration thus measured is sent through the output line 36a to the controller 38. On this basis, the controller 38 calculates the optimal sterilizing conditions and controls the hydrochloric acid constant rate pump 4 and the power source 6 through the output lines 4a and 6a, and the cooling water is sterilized so as to prevent the proliferation of germs. The embodiment depicted in FIG. 6 is more effective than when conventional electrolytic cells are used in that the cooling water pH or available chlorine concentration can be controlled, thereby allowing mechanical corrosion to be suppressed.

Another embodiment featuring the use of the apparatus in FIG. 5 is described below. The example of the sterilization of a water storage tank as depicted in FIG. 7 can be given. FIG. 7 is a diagram depicting an example of a water storage tank equipped with the sterilizing apparatus in FIG. 5. In FIG. 7, most of the structural elements are the same as those in the apparatus depicted in FIG. 6, as indicated by symbols that are the same as those in FIG. 6, and these will not be discussed in further detail.

In FIG. 7, a water storage tank 39 is equipped with circulation piping 37, and the circulation piping 37 is equipped with a pump 35, the sterilizing apparatus in FIG. 5, and a chlorine concentration meter 36.

The operation of the apparatus in FIG. 7 is described below. The raw water W2 in the water storage tank 39 is circulated by the pump 35 through the circulation piping 37 in the direction indicated by the arrow Y. The chlorine concentration of the raw water W2 is measured by the chlorine concentration meter 36, and sterilization is effected by the sterilizing apparatus in the same manner as in FIG. 6. That is, the raw water W2 in the water storage tank 39 can be sterilized, and the proliferation of germs can be freely controlled. In this case, the available chlorine concentration in the water storage tank 39 may be controlled by the controller 38 to optimal levels.

The water storage tank in FIG. 7 may be used, for example, for baths, pools, water tanks, fish ponds, and the like. When used for baths, the circulation piping 37 should be equipped with a filter apparatus and heating apparatus. When used for pools, the invention is more effective than methods of directly blowing chlorine into water and methods for injecting sodium hypochlorite into water because the bactericidal potency is greater, the equipment is simpler, and there is no need to handle chlorine gas.

In all the examples given above, it is clear that all of the aforementioned problems 1) through 3) of conventional electrolytic cells are remedied, and it can be understood that the present invention is extremely effective.

In conventional electrolytic cells, electrolytic treatment is often carried out by mixing a salt such as sodium chloride with the raw water to increase the electrolytic efficiency, but in the present invention, efficient electrolytic treatment can be carried out even with hydrochloric acid-containing raw water that contains no salts. In cases involving the use of such hydrochloric acid-containing raw water that contains no salts, an advantage is that no salts are precipitated in the form of solids during the use of the electrolytically treated liquid. That is, no salts adhere to the interior of the cooling tower 33 in FIG. 6, and no salts adhere to the wall surface of the water storage tank 39. When hydrochloric acid-containing raw water that contains no salts is thus used, the present invention has far better effects than those obtained in the past.

KEY TO THE FIGURES

Figure 1:
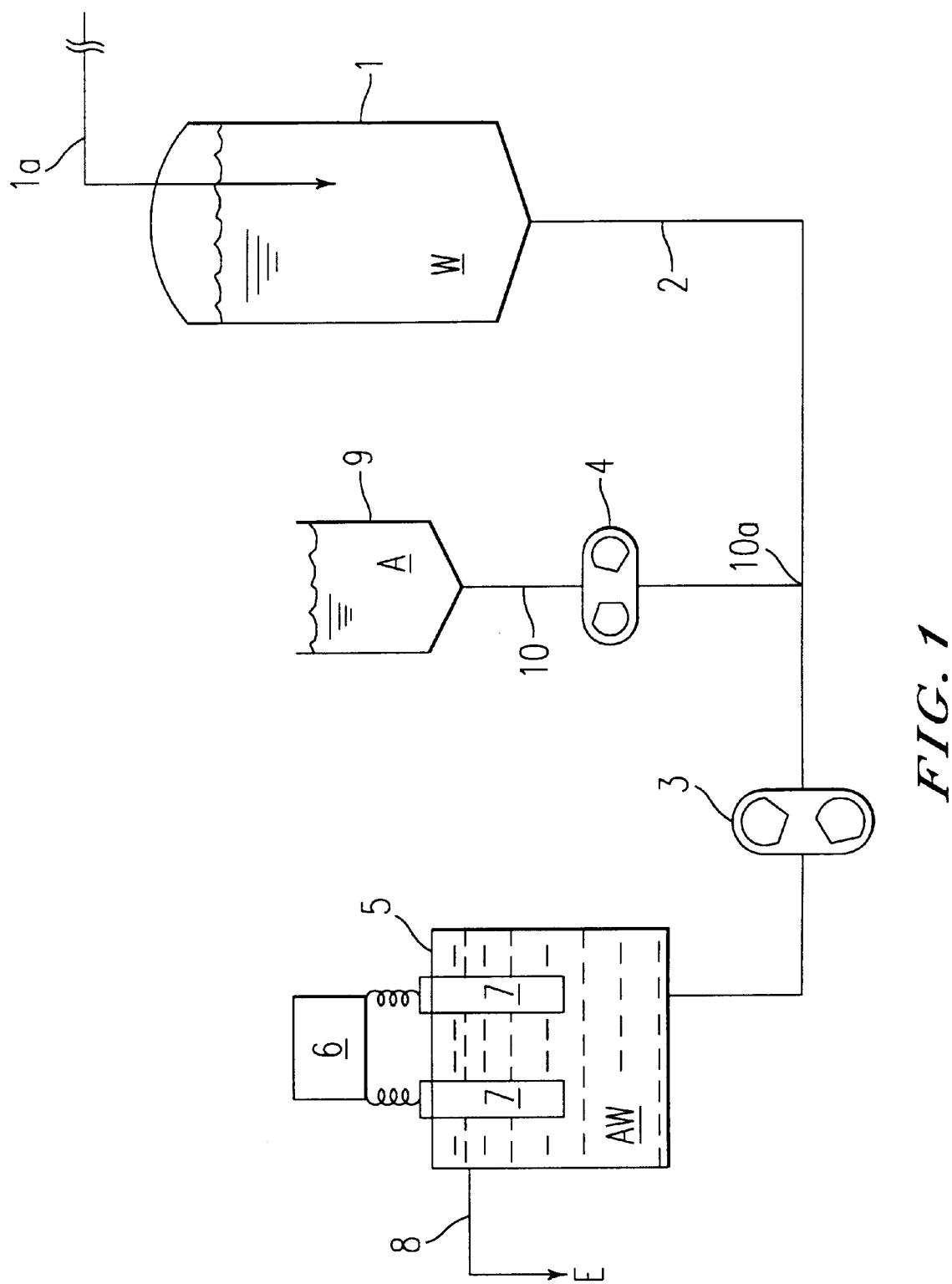
FIG. 1 is an example of the apparatus pertaining to the present invention.

1: raw water tank; 1a: raw water supply pipe; 2: raw water transport pipe; 3: raw water pump; 4: hydrochloric acid constant rate pump; 5: electrolytic cell; 6: power source; 7: electrode; 8: electrolytically treated liquid discharge pipe; 9: hydrochloric acid tank; 10: hydrochloric acid supply pipe; 11: bactericide transport pump; 12: diluting water transport pipe; 12a: junction point; 13: flow rate regulating valve; 14: container; 15: hydrochloric acid-containing raw water pipe; 16: orifice; 17: diluting water source; 18: constant flow rate valve; 19: ejector; 20: apparatus for manufacturing bactericide; 21: float valve; 22: float; 23: cistern; 24: flushing water transport pipe; 25: toilet; 30: sterilizing apparatus; 31: flow rate regulating valve; 32: flow rate regulating valve; 33: cooling tower; 34: condenser; 35: pump; 36: chlorine concentration meter; 37: circulation piping; 38: controller; 39: water storage tank; A: hydrochloric acid; W: raw water; AW: hydrochloric acid-containing raw water; E: electrolytically treated liquid; Ed: bactericide; WO: flushing water; W1: raw water; W2: raw water.

The present invention is described in detail below with reference to test examples.

TEST EXAMPLE 1

This test was conducted to check the relation between frequency and bactericidal effects when the electrolytic treatment was carried out using a rectangular wave alternating current power source.

1) Sample Preparation

Bactericide samples were produced by the same method as that in Example 4 described below using the apparatus described in Example 3 below except that the raw water flow rate was adjusted to 900 mL/min, the number of revolutions of the raw water pump 3 and hydrochloric acid constant rate pump 4 were adjusted so as to adjust the pH of the raw water containing hydrochloric acid to 2.4, and the alternating current power supply used to provide electricity was changed to 14 A, with the frequency varied in stages from 0.5 Hz to 10 Hz.

2) Test Methodology

The bactericidal effects of the bactericides obtained under varying conditions were tested by the following method. 50 mL common sterile bouillon medium (by Eiken Kagaku) was inoculated with 1 platinum loop of $E.\ coli$ ((IID) 0111 line, by Tokyo Daigaku Ikagaku Kenkyujo) and cultured for 20 hours at 37° C., and 1 mL of the resulting broth (cell number: $11 \times 10^6$/mL) was added and mixed to homogeneity with 99 mL of varying bactericide samples, the mixtures were allowed to stand for 2 minutes at room temperature, and then the cell number (N) of the mixtures was determined by a common method (Tomokichi Tsugo et al, editors, Nyugyo Handobukku, pp. 513–514, published by Asakura Shoten (1973)). The cell number ($N_0$) of controls similarly tested using sterile physiological saline instead of the bactericide samples was also determined.

The ratio of the cell number of the bactericides to the cell number of the control ($N_0/N$) was calculated, and this ratio was given in terms of logarithmic value in the testing of the bactericidal effects.

3) Test Results

The results are given in Table 1. It is apparent in Table 1 that bactericidal effects were obtained with samples at a frequency of 5 Hz or less, and that extremely potent bactericidal effects were obtained with samples at a frequency of 2 Hz or less. It was thus concluded in the present invention that the frequency of the alternating current should be no more than 5 Hz, and preferably no more than 2 Hz. Bactericides pertaining to the present invention were similarly tested with other apparatus and producing methods, but virtually the same results were obtained.

TABLE 1

| | Frequency (Hz) | | | | | |
|---|---|---|---|---|---|---|
| Test Parameters | 0.5 | 1 | 2 | 4 | 5 | 10 |
| Bactericidal effects (log $N_0/N$) | >7.04 | >7.04 | >7.04 | 1.18 | 1.74 | 0.74 |

TEST EXAMPLE 2

This test was conducted to check the relation between the quantity of electrolytic electricity and bactericidal effects when the electrolytic treatment was carried out using a direct current power source.

1) Sample Preparation

Bactericide samples were produced by the same method as that in Example 4 described below except that the raw water flow rate was adjusted to 900 mL/min, the number of revolutions of the raw water pump 3 and hydrochloric acid constant rate pump 4 were adjusted so as to adjust the pH of the raw water containing hydrochloric acid to 2.6, and direct current was used to provide electricity, with the quantity of electrolytic electricity varied in stages from 0.27 c/mL to 1.3 c/mL, as shown in Table 2.

2) Test methodology

The bactericidal effects of the bactericides were tested by the same method as in Test Example 1.

3) Test Results

The results are given in Table 2. It is apparent in Table 2 that bactericidal effects were obtained with samples at an electrolytic electrical quantity of 0.4 c/mL or more, and that extremely potent bactericidal effects were obtained with samples at an electrolytic electrical quantity of 0.8 c/mL or more. It was thus concluded that in the electrolytic treatment of the present invention, the electrolytic electrical quantity should be at least 0.4 c/mL, and preferably at least 0.8 c/mL. Bactericides pertaining to the present invention were similarly tested with other apparatus and manufacturing methods, but virtually the same results were obtained.

TABLE 2

| Test Parameters | Current (c/mL) | | | | | |
|---|---|---|---|---|---|---|
| | 0.27 | 0.33 | 0.40 | 0.53 | 0.80 | 1.30 |
| Bactericidal effects (log $N_0/N$) | 1.56 | 1.67 | 2.20 | 5.14 | >6.90 | >6.90 |

TEST EXAMPLE 3

This test was conducted to check the relation between the available chlorine concentration of bactericides and their bactericidal effects.

1) Sample Preparation

Bactericide samples were prepared by the same method as that in Example 4 described below except that the raw water flow rate was adjusted to 470 mL/min, and the available chlorine concentration was varied by using direct current to provide electricity, with the quantity of electrolytic electricity varied in stages.

The resulting samples were suitably diluted, and the available chlorine concentration was quantified by the iodine method (edited by Nihon Igakkai, Eisei Shikenho (Chukai, p. 1066, published by Kanahara Shuppan (1990)) to obtain a group of samples in which the available chlorine concentration was varied in stages from 0.05 to 6.4 ppm. The pH of the samples was uniform at about 5.

2) Test methodology

The bactericidal effects of the bactericides were tested by the same method as in Test Example 1.

3) Test Results

The results are given in Table 3. It is apparent in Table 3 that the bactericidal effects diminished with samples having an available chlorine concentration of less than 0.1 ppm. It was thus concluded that in the manufacturing method of the present invention, the bactericides should be used with an available chlorine concentration of at least 0.1 ppm. Bactericides pertaining to the present invention were similarly tested with other apparatus and manufacturing methods, but virtually the same results were obtained.

TEST EXAMPLE 4

This test was conducted in order to examine the relation between the value of voltage to be applied onto the electrolytic cell and the kind of a gas to be generated.

1) Preparation of a Sample

A sample of a bactericide was prepared in the same manner as in Example 9 to be described later except that the voltage to be applied onto the electrolytic cell was raised gradually from 0 volt.

2) Method of the Test a) The obtained bactericide was collected and diluted with water, and then the amount of chlorine thereof was measured by iodometry.

b) The bactericide discharged from the electrolytic cell was introduced into a high-concentration sodium hydroxide solution stored in a scrubbing bottle, the gas which was not absorbed in the high-concentration sodium hydroxide solution but discharged was collected and introduced into an $O_2$ sensor, and the amount of oxygen thereof was measured.

c) After the completion of the measurement of the amount of oxygen in the above b), a wet potassium iodide starch test paper was exposed to the gas, and ozone was detected and measured by iodometry.

3) Results of the Test

Figure 8:
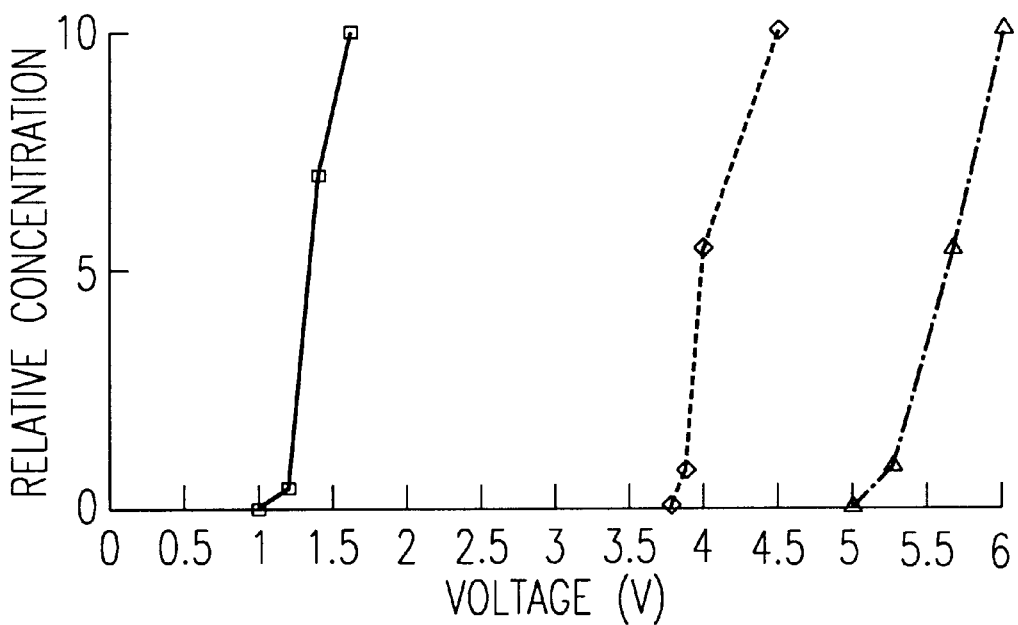
FIG. 8 is a graph showing the relation between the value of voltage to be applied onto the electrolytic cell and the kind of a gas to be generated.

The results of the test are show in FIG. 8. FIG. 8 is a graph showing the relation between the value of voltage to be applied onto the electrolytic cell and the kind of the gas generated. The transverse axis of FIG. 8 shows voltage, and the ordinate axis shows the amount of the gas generated. However, the scale of the transverse axis shows the value of voltage between neighboring pair electrodes, and the numerical value of the ordinate axis shows the rate of the gas generated in the case that the maximum amount of the gas generated is made 10.

In FIG. 8, ■ shows the measured value of chlorine, ♦ shows that of oxygen, and ▲ shows that of ozone.

As is apparent from FIG. 8, chlorine begins to occur at a voltage of more than 1.3 volts, and the amounts attains the maximum at a voltage of more than 1.5 volts. Oxygen begins to occur at a voltage of more than 3.9 volts, and the amount attains the maximum at a voltage of 4.3 volts. Ozone beings to occur when the voltage exceeds 5.0 volts, and the amount attains the maximum at a voltage of 6.0 volts.

It is apparent, accordingly, that chlorine begins to occur at a voltage of more than 1.3 volts and that when the voltage exceeds 3.9 volts, wasteful oxygen or ozone occurs. As the results of the test, it is revealed that the value of voltage between neighboring pair electrodes is preferably more than 1.3 volts and less than 3.9 volts.

TEST EXAMPLE 5

This test was conducted in order to examine the relation between the value of voltage between neighboring pair electrodes and electric power efficiency.

1) Preparation of a Sample

A sample of a bactericide was prepared in the same manner as in Example 9 to be described later except that the value of voltage between neighboring pair electrodes was raised gradually from 1.5 volts.

2) Method of the Test

The obtained bactericide was collected and diluted with water, and then the amount of chlorine thereof was measured by iodometry. In addition, the value of electric power efficiency was calculated by calculating electric power from the electric current and the voltage at the time of measurement and dividing the amount of chlorine generated by the electric power.

3) Results of the Test

Figure 9:
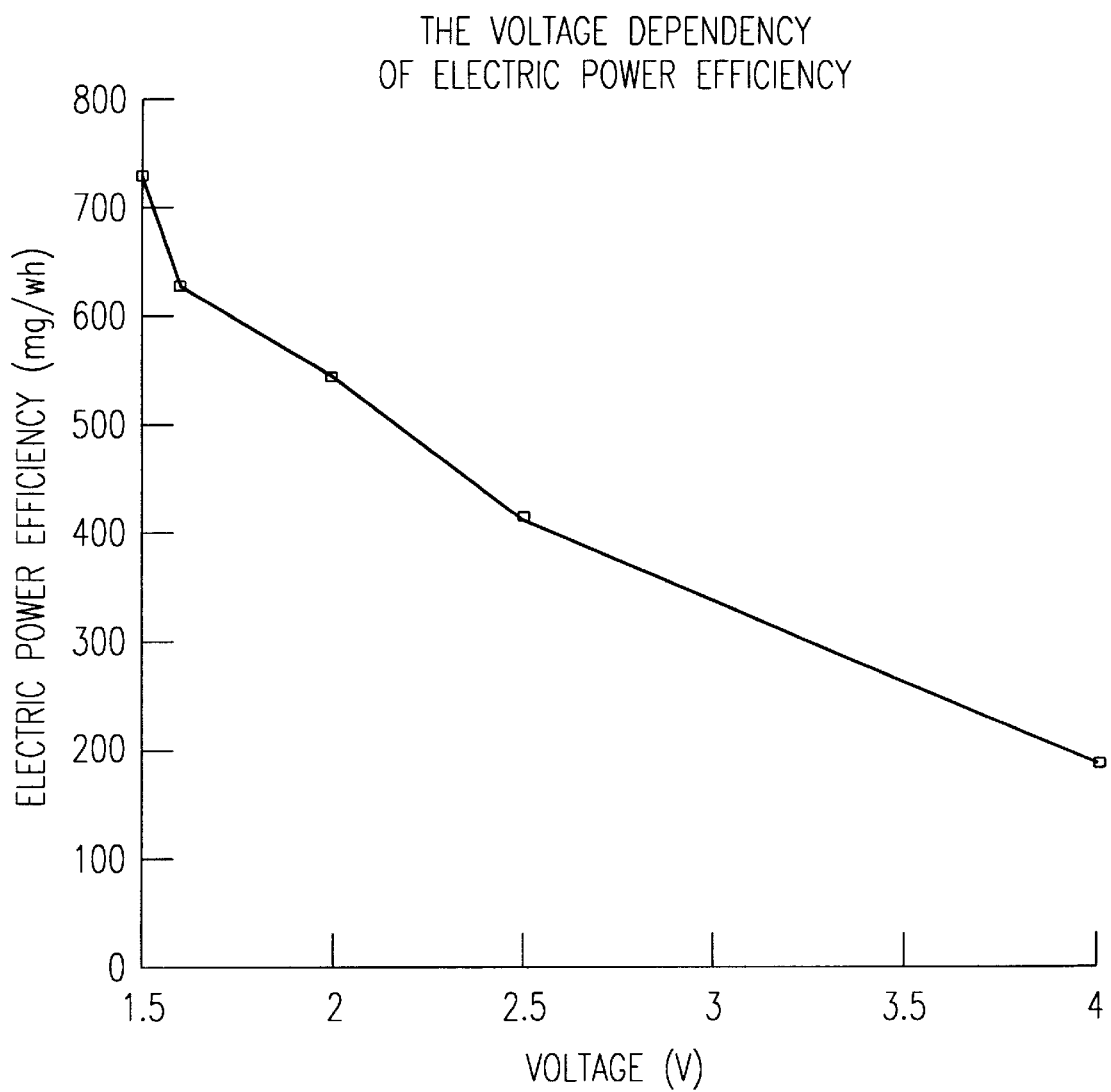
FIG. 9 is a graph showing the relation between the value of voltage to be applied onto the electrolytic cell and electric power efficiency.

The results of the test are as shown in FIG. 9. FIG. 9 is a graph showing the relation between the value of voltage to be applied onto the electrolytic cell and electric power efficiency. The transverse axis of FIG. 9 shows the value of voltage between neighboring pair electrodes, and the ordinate axis shows the electric power efficiency.

As is apparent from FIG. 9, the smaller the value of voltage applied onto the electrolytic cell is, the larger becomes the electric power efficiency. Since it is revealed from the results of Test Example 4 that if the voltage is less than 1.5 volts, the amount of chlorine generated decreases, it is finally revealed from the results of this test that electrolysis is preferably conducted at a low voltage possible of more than 1.5 volts in the method of the present invention.

TABLE 3

| Test Parameters | Available chlorine concentration (ppm) | | | | | | | |
|---|---|---|---|---|---|---|---|---|
| | 0.05 | 0.10 | 0.20 | 0.50 | 1.00 | 2.00 | 3.10 | 6.40 |
| Bactericidal effects (log $N_0/N$) | 2.50 | >5.70 | >5.70 | >5.70 | >5.70 | >5.70 | >5.70 | >5.70 |

BEST MODE FOR CARRYING OUT THE INVENTION

The present invention is described below in further detail with reference to examples, but the present invention is not limited in any way to the following examples.

EXAMPLE 1

FIG. 1 depicts an example of the manufacturing apparatus pertaining to the present invention. The structural elements and operation of the apparatus in FIG. 1 were described above as a preferred embodiment.

Raw water tank 1: 100 L vinyl chloride tank by Hokuetsu Giken Kogyo

Raw water pump 3: SL-35SFD by Erepon

Hydrochloric acid tank 9: by Hokuetsu Giken Kogyo

Hydrochloric acid constant rate pump 4: CRM-04, by Erepon

Electrolytic cell 5: by Hokuetsu Giken Kogyo; distance between electrodes: 2 mm; electrode surface area: 5000 cm$^2$; no diaphragm Electrode 7: by Hokuetsu Giken Kogyo, platinum-coated titanium net Power source: SM93-1280, by Chuo Seisakusho Electrolytically treated liquid discharge pipe 8: by Hokuetsu Giken Kogyo

EXAMPLE 2

This example is of a method for manufacturing a bactericide using the manufacturing apparatus in Example 1 above, the details of which are described with reference to FIG. 1.

The apparatus was first pre-operated in the following manner, which comprise supplying raw water by the raw water pump 3 from the raw water tank 1 containing raw water (well water) to the electrolytic cell 5 at a rate of 1000 L/hr, adding hydrochloric acid as standardized food additive (36.46%, by Junsei Kagaku) continuously by means of the hydrochloric acid constant rate pump 4 from the hydrochloric acid tank 9 where it was stored to the raw water to experimentally prepare raw water containing hydrochloric acid, collecting the prepared raw water containing hydrochloric acid, measuring the pH of the same, and adjusting the number of revolutions of the hydrochloric acid constant rate pump 4 to adjust the pH of the raw water containing hydrochloric acid to 2.5.

Based on the conditions established by the aforementioned pre-testing, a bactericide was produced by the steps which comprise supplying raw water by the raw water pump 3 from the raw water tank 1 containing the raw water to the electrolytic cell 5 at a rate of 1000 L/hr, adding hydrochloric acid as standardized food additive (36.46%, by Junsei Kagaku) continuously by means of the hydrochloric acid constant rate pump 4 from the hydrochloric acid tank 9 where it was stored to the raw water to prepare hydrochloric acid containing raw water with a pH of 2.5, which was continuously introduced to the electrolytic cell 5, applying alternating current with a frequency of 2 Hz at a rate of 0.8 Coulombs per milliliter hydrochloric acid-containing raw water to the electrodes immersed in the hydrochloric acid-containing raw water, treating the raw water containing hydrochloric acid electrolytically, recovering the electrolytically treated liquid from the electrolytically treated liquid discharge pipe 8, and obtaining a bactericide with a pH of 2.5 and a redox potential of 1130 mV continuously at a rate of about 1000 L/hour.

A test of the resulting bactericide by the same method as in Test Example 1 revealed a log ($N_0/N$) of 7.0 or more, indicating pronounced bactericidal effects.

EXAMPLE 3

Another embodiment of the manufacturing apparatus pertaining to the present invention is described. The embodiment of the structural elements was the same as that in Example 1 above (the same structural elements are designated by the same symbols as in FIG. 1 and will not be further indicated). The apparatus in this example was equipped with the following devices.

Raw water pump 3: 7553-70 by Colepalmer

Hydrochloric acid constant rate pump 4: SJ-1211 H by Ato Electrolytic cell 5: MARK-IL by Yuasa Ionix (distance between electrodes: 2 mm; no diaphragm)

Power source: selectable arrangement of direct current power source (PAK 35-20A by KikumizU Denki) and rectangular wave alternating current power source (two direct current power sources S82D-3024 by Omuron to produce ±24 V, convertible to any frequency)

Other than the above parts, the same apparatus as in Example 1 above was used.

EXAMPLE 4

This example is of a method for manufacturing a bactericide using the manufacturing apparatus in Example 3 above, the details of which are described with reference to FIG. 1.

The apparatus was first pre-operated in the following manner, which comprise supplying raw water by the raw water pump 3 from the raw water tank 1 containing raw water (well water) to the electrolytic cell 5 at a rate of 130 L/hr, adding first class hydrochloric acid (by Kanto Kagaku) continuously by means of the hydrochloric acid constant rate pump 4 from the hydrochloric acid tank 9 where it was stored to the raw water to experimentally prepare raw water containing hydrochloric acid, collecting the prepared raw water containing hydrochloric acid to measure the pH of the same, and adjusting the number of revolutions of the hydrochloric acid constant rate pump 4 to adjust the pH of the raw water containing hydrochloric acid to 1.45.

Based on the conditions established by the aforementioned pre-testing, a bactericide was produced by the steps which comprise supplying raw water by the raw water pump 3 from the raw water tank 1 containing the raw water to the electrolytic cell 5 at a rate of 130 L/hr, adding first class hydrochloric acid (by Kanto Kagaku) continuously by means of the hydrochloric acid constant rate pump 4 from the hydrochloric acid tank 9 where it was stored to the raw water to prepare hydrochloric acid-containing raw water with a pH of 1.45, which was continuously introduced to the electrolytic cell 5, applying direct current at a current of 21 A and a voltage of 6.3 V to the electrodes immersed in the hydrochloric acid-containing raw water, treating the raw water containing hydrochloric acid electrolytically, recovering the electrolytically treated liquid from the electrolytically treated liquid discharge pipe 8, and obtaining a bactericide with a pH of 1.45 and a redox potential of 1170 mV thus recovered.

The resulting bactericide was diluted 10-fold with well water to obtain sterilized water with a pH of 2.55 and a redox potential of 1135 mV.

A test of the resulting bactericide and sterilized water by the same method as in Test Example 1 revealed a log $(N_0/N)$ of 7.0 or more, indicating pronounced bactericidal effects.

The bactericide obtained in Example 4 was diluted 20-fold with well water to obtain sterilized water with a pH of 5.1. The available chlorine concentration of the sterilized water was 3.0 ppm. A test of the 20-fold diluted sterilized water by the same method as in Test Example 1 revealed a log $(N_0/N)$ of 7.0 or more, indicating pronounced bactericidal effects.

The aforementioned 10-fold diluted sterilized water and 20-fold diluted sterilized water were introduced into containers and stored for 3 days while shielded from light at room temperature, and a test of the bactericidal effects by the same method as in Test Example 1 revealed a log $(N_0/N)$ of 5.3 in the 10-fold diluted sample and 7.0 or more in the 20-fold diluted sample. It was thus concluded that the bactericidal effects could be kept longer after dilution at a pH of 5.1.

Similar testing of sterilized water with varying degrees of dilution and varying pH levels revealed less deterioration in the bactericidal effects over time at a pH or 7.0 or less after dilution, and especially between 3.5 and 6.5.

EXAMPLE 5

Figure 2:
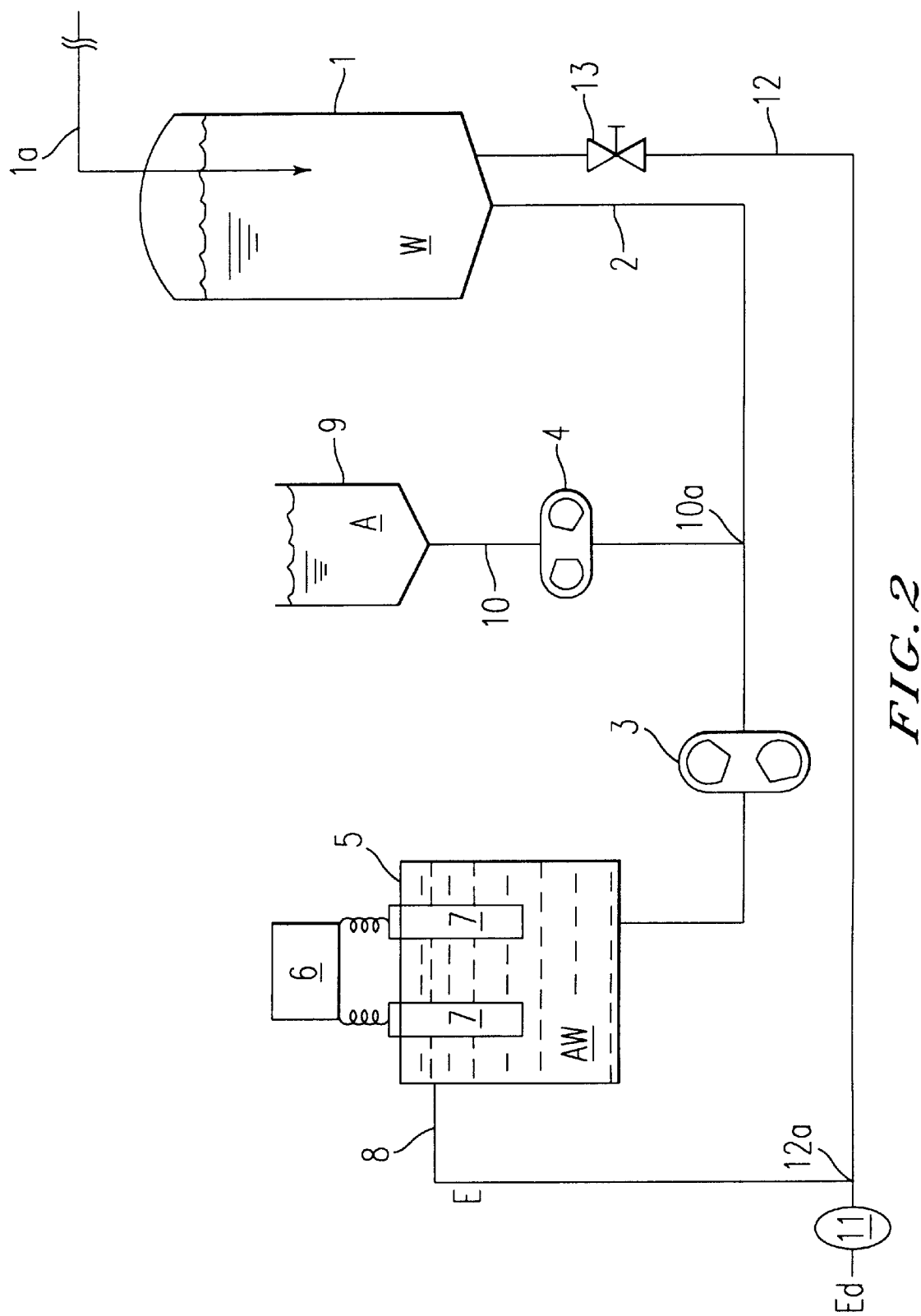
FIG. 2 is another example of the apparatus pertaining to the present invention.

Another embodiment of the apparatus pertaining to the present invention is described. FIG. 2 depicts another embodiment of the apparatus pertaining to the present invention. The embodiment of the structural elements of the apparatus in FIG. 2 was the same as that in Example 1 above, as indicated by the same symbols as those used in FIG. 1, which will not be discussed in further detail.

The devices in the apparatus depicted in FIG. 2 were essentially the same as those in Example 3 above, with the following devices added.

Bactericide transport pump 11: MD-30R centrifugal pump by Iwaki

Flow rate regulating valve 13: manual type by Towa Techno

The structural elements and operation of the apparatus in FIG. 2 were described above as a preferred embodiment.

Because a centrifugal pump was used as the bactericide transport pump 11, the electrolytically treated liquid and diluting water could be stirred after being mixed together.

EXAMPLE 6

This example is of a method for manufacturing a bactericide using the manufacturing apparatus in Example 5 above, the details of which are described with reference to FIG. 2.

The apparatus was first pre-operated in the following manner which comprise supplying raw water by the raw water pump 3 from the raw water tank 1 containing raw water (well water) to the electrolytic cell 5 at a rate of 130 L/hr, and adjusting the pH of the raw water containing hydrochloric acid to 1.45 by the same procedure as in Example 4 above.

Then, by the same procedure as in Example 4 above, hydrochloric acid-containing raw water with a pH of 1.45 prepared was continuously introduced into the electrolytic cell 5, and the raw water containing hydrochloric acid was electrolytically treated.

The centrifugal pump 11 was operated to control the flow rate regulating valve 13, and diluting water was transported at a rate of 1170 L/hr from the raw water tank 1 to the junction point 12a, and was mixed and diluted with the electrolytically treated liquid discharged from the electrolytically treated liquid discharge pipe 8. The diluting water and electrolytically treated liquid flow rate ratio was 9 to 1. A bactericide with a pH of 2.55 and a redox potential of 1135 mV was thus obtained.

A test of the resulting bactericide by the same method as in Test Example 1 revealed a log $(N_0/N)$ of 7.0 or more, indicating pronounced bactericidal effects.

EXAMPLE 7

Figure 3:
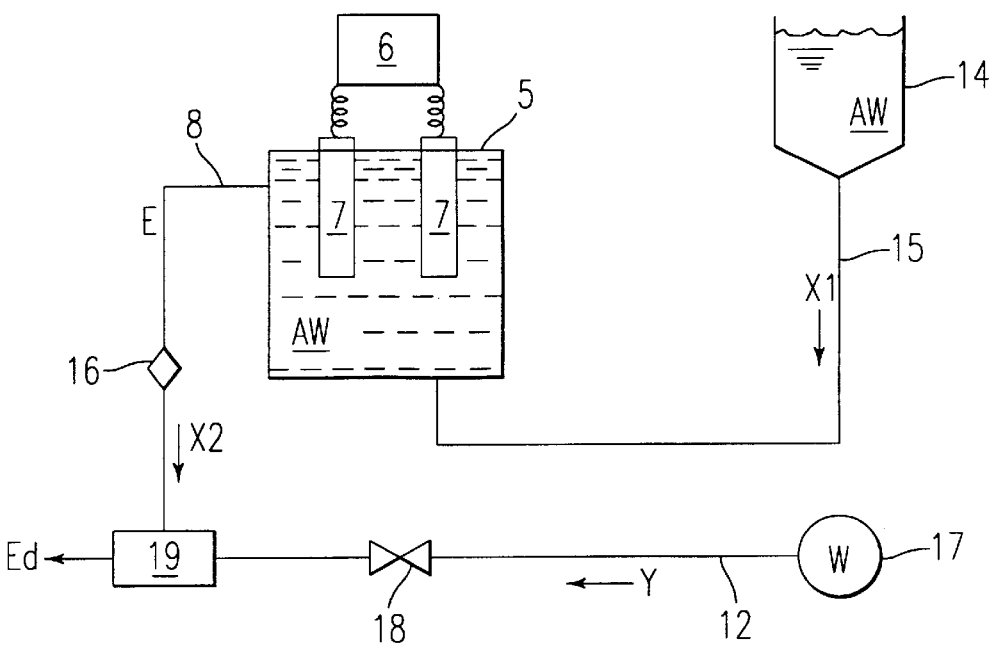
FIG. 3 is another example of the apparatus pertaining to the present invention.
Figure 4:
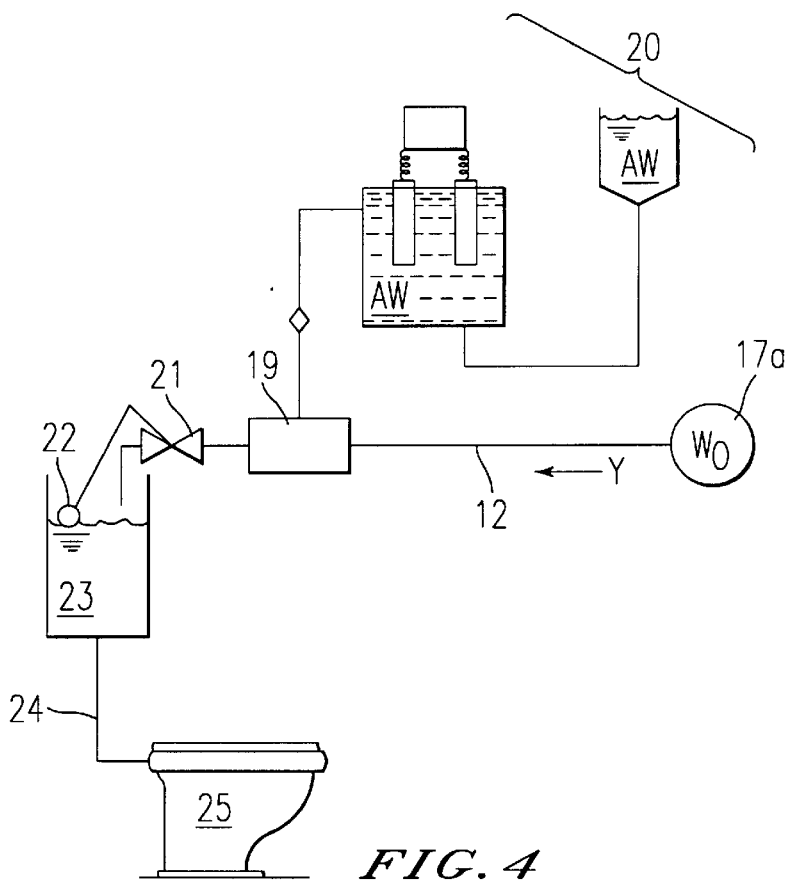
FIG. 4 depicts a flush toilet featuring the use of the apparatus in FIG. 3.

Another embodiment of the apparatus pertaining to the present invention is described. FIG. 3 depicts another embodiment of the apparatus pertaining to the present invention. The structural elements and operation of the apparatus in FIG. 3 were described above in the form of a preferred embodiment.

Container (means for storing raw water containing hydrochloric acid) 14: made of polyethylene terephthalate Electrolytic cell 5: by our own made Electrode 7: 20×85 platinum-plated titanium; distance between electrodes: 2 mm Power source 6: S8E1-O15O5 by Omuron Constant flow rate valve 18: 0651A by Kakudai Orifice 16: fine Teflon tube, 1 mm in diameter Ejector 19: polyethylene water pump Diluting water source 17: public water utility The device depicted in FIG. 3 had a simple structure because the diluting water 17 was merely connected to a household water faucet, making it suitable primarily for use in common households, factories, restaurants, and the like. Advantages are that the unit has no moving components such as rotating pumps, is inexpensive, and is easily inspected for maintenance purposes. It is also small and lightweight, making it easy to transport.

EXAMPLE 8

This example is of a method for manufacturing a bactericide using the manufacturing apparatus in Example 7 above, the details of which are described with reference to FIG. 3.

Hydrochloric acid as standardized food additive (36.46% by Junsei Kagaku) was diluted with distilled water to prepare raw water containing hydrochloric acid in an amount of 0.1 mol/L, and the raw water was stored in a container 14.

The tap water faucet serving as the diluting water source 17 was turned on to flow the diluting water to the ejector 19, with adjusting the flow rate by the constant flow rate valve 18 to adjust the flow rate at the outlet of the ejector 19 to 1.5 L/min. The flow rate of the hydrochloric acid-containing raw water and the electrolytically treated liquid flowing through the hydrochloric acid-containing raw water pipe 15, electrolytic cell 5, and electrolytically treated liquid discharge pipe 8 was 50 mL/min.

A direct current was applied to the electrodes in the electrolytic cell 5, and the raw water containing hydrochloric acid was electrolytically treated, allowing a bactericide with a pH of 3.4 to be continuously obtained at a capacity of 2.5 L/min.

Tests of the resulting bactericide by the same method as in Test Example 1 revealed pronounced bactericidal effects.

The 0.1 mol/L hydrochloric acid-containing raw water prepared in Example 8 had high handling stability and was safe for household use.

TEST EXAMPLE 6

This test was conducted in order to examine the relation between the number of cells divided by the unwired electrode provided in the electrolytic cell connected in series and the electric power efficiency about the chlorine generated.

1) Preparation of a Sample

A sample of a bactericide was prepared in the same manner as in Example 9 to be described later except that the test was conducted varying the number of cells divided by the unwired electrode provided in the electrolytic cell connected in series and that the voltage to be applied onto the electrolytic cell was set to a value of voltage between neighboring pair electrodes of 2 volts.

2) Method of the Test

The obtained bactericide was collected and diluted with water, and then the amount of chlorine thereof was measured by iodometry. In addition, the value of electric power efficiency was calculated by calculating electric power from the electric current and the voltage at the time of measurement and dividing the amount of chlorine generated by the electric power.

3) Results of the Test

Figure 10:
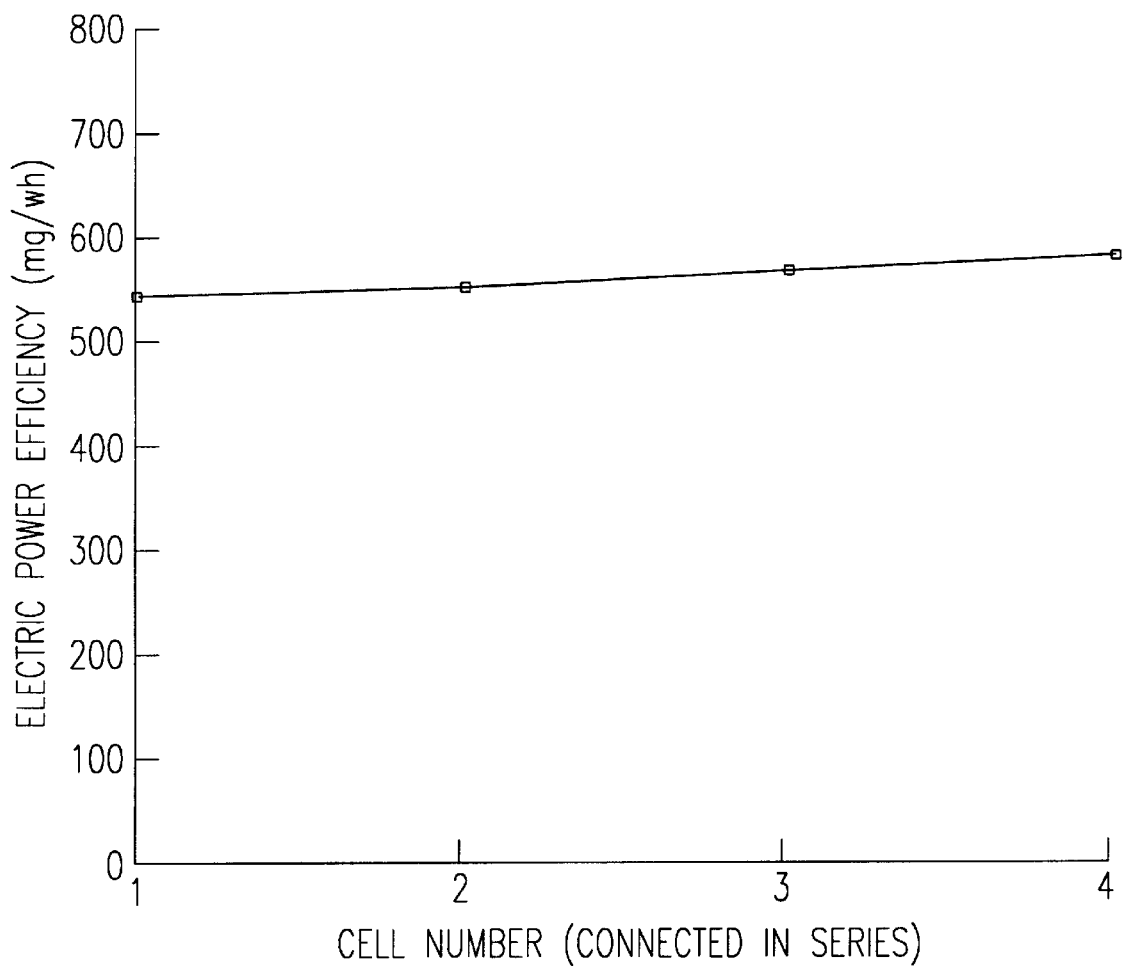
FIG. 10 is a graph showing the relation between the number of cells divided by the unwired electrode provided in the electrolytic cell and electric power efficiency.

The results of the test are as shown in FIG. 10. FIG. 10 is a graph showing the relation between the number of cells divided by the unwired electrode provided in the electrolytic cell and the electric power efficiency. The transverse axis of FIG. 10 shows the number of cells formed by the unwired electrode, and the ordinate axis shows the electric power efficiency. Regarding the transverse axis, when there exists no unwired electrode, the number of cell is 1, when there exists one unwired electrode, the number of cells is 2, when there exist two unwired electrodes, the number of cells is 3, and when there exist three unwired electrodes, the number of cells is 4.

As is apparent from FIG. 10, the larger the number of the unwired electrodes is, the larger becomes the electric power efficiency. It is revealed from the results of this test that, in the present invention, the larger the number of the unwired electrodes in the electrolytic cell connected in series is, the better is it.

EXAMPLE 9

Figure 11:
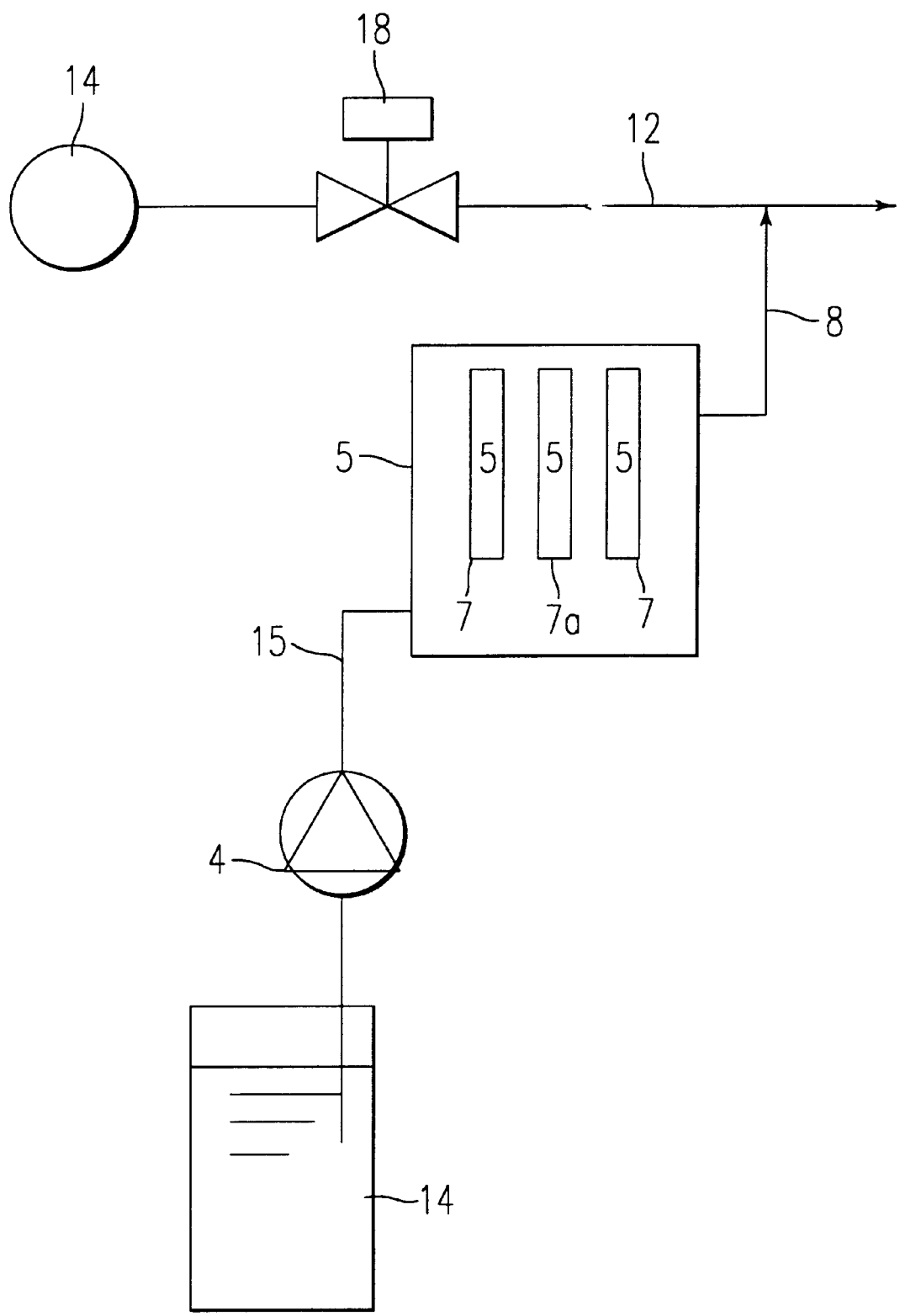
FIG. 11 is a diagram showing one embodiment of an apparatus for performing the method for manufacturing a bactericide according to the present invention.

The apparatus for manufacturing the bactericide shown in FIG. 11 was produced by modifying the apparatus shown in FIG. 3. FIG. 11 is a diagram showing one embodiment of an apparatus for performing the method for manufacturing a bactericide according to the present invention.

In FIG. 11, the elements common in FIG. 1 through FIG. 3 are shown with the same marks to omit detailed description.

Electrolytic cell 5: Cell connected in series

Electrode 7, 7a: Platinum-plated titanium available area is 0.24 dm$^2$.

Constant flow rate valve 18: HCT15A

The electrolytic cell 5 employs five electrodes 7 and five electrodes 7a, but the detailed illustration thereof is omitted in FIG. 11. Regarding the five electrodes 7 and five electrodes 7a, the central one is connected to the cathode of the electric source to form a cathode, and two electrodes at both ends are connected to the anode of the electric source to form an anode. Hence, the number of the unwired electrodes 7a is 2 in total, and substantially, two sets of two electrolytic cells connected in series are connected in parallel.

In the vessel 14 was stored 3% (by weight) of hydrochloric acid to use as hydrochloric acid-containing raw water. The hydrochloric acid-containing raw water was let to run into a hydrochloric acid-containing raw water pipe 15 by a quantitative pump 4 at a flow of 120 mL/h and introduced into the electrolytic cell 5.

In the electrolytic cell 5, a voltage of 4.2 V and an electric current of 2.5 A were applied onto the electrodes 7 and 7a. In this case, the voltage between neighboring pair electrodes is 2.1 V.

The water was let to run into a diluted water pipe 12 at a flow of 240 l/h, and the electrolytically treated liquid was diluted to obtain a bactericide with an effective chlorine concentration of 14 ppm.

EXAMPLE 10

Figure 5:
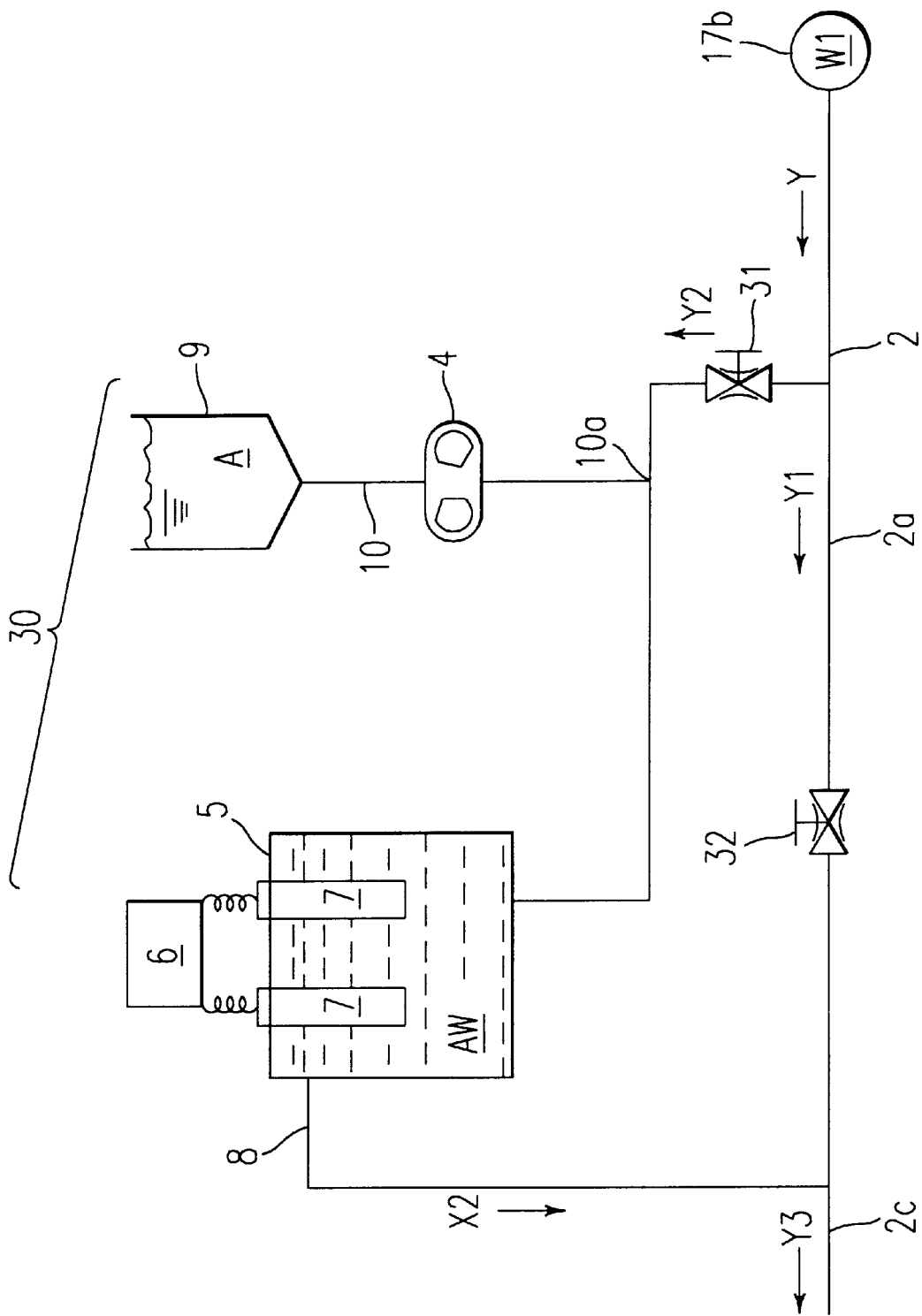
FIG. 5 is an example of a sterilizing apparatus for implementing the method of sterilization pertaining to the present invention.
Figure 6:
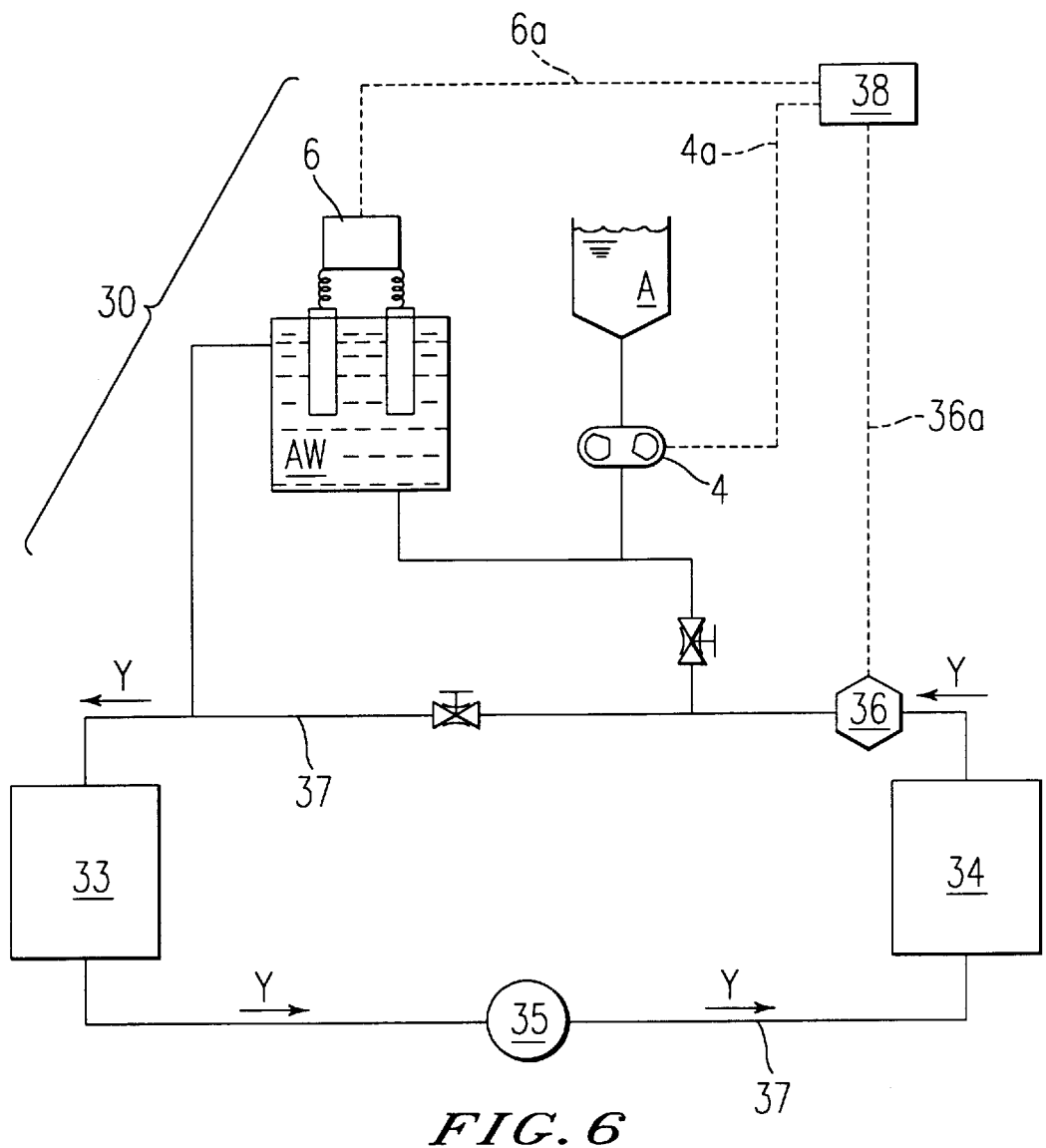
FIG. 6 is an example of cooling water circulation piping for a cooling tower equipped with the sterilizing apparatus in FIG. 5.
Figure 7:
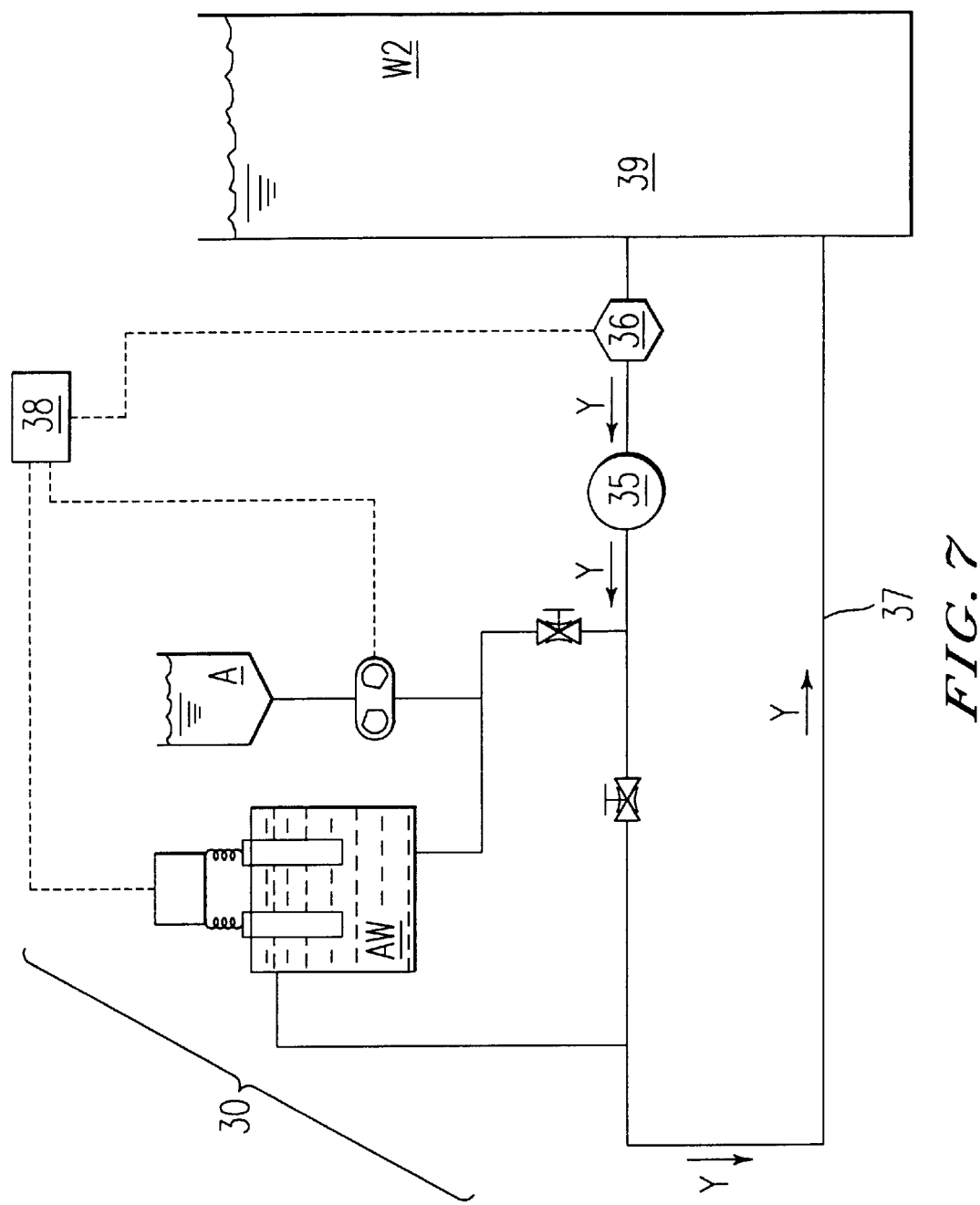
FIG. 7 is an example of a water storage tank equipped with the sterilizing apparatus in FIG. 5.

The apparatus shown in FIG. 5 was modified as below. That is, the electrolytic cell 5 was altered to the electrolytic cell connected in series 5. In the electrolytic cell connected in series 5, the electrode 7 employed the same material as in Example 9 and the available area per one was made 2.3 dm$^2$. Seventeen electrodes 7 were arranged at an interval of 3 mm, and every other electrode was connected to the electric source. Thereby, the electrolytic cell connected in series 5 similar to eight electrolytic cells connected in series arranged in parallel was constituted.

Other apparatus are as below:

Constant flow rate valve 18: HCT15A

Hydrochloric acid constant rate pump 4: EH-B10VC-200R2

The water was let to run into the raw water pipe 2 at a flow of 10000 l/h. The water was let to run into the raw water pipe 2b at a flow of 6 l/h.

In the hydrochloric acid tank 9 was stored 21% (by weight) of hydrochloric acid, and the hydrochloric acid was let to run into the raw water pipe 2b by the quantitative pump 4 at a flow of 800 mL/h and introduced into the electrolytic cell 5.

In the electrolytic cell 5, a voltage of 4.6 V and an electric current of 105 A were applied onto the electrode 7. In this case, the voltage between neighboring pair electrodes is 2.3 V.

The electrolytically treated liquid was returned into the raw water pipe 2b and a bactericide with an effective chlorine concentration of 14 ppm could be obtained at a flow of 10000 l/h.

INDUSTRIAL APPLICABILITY

As described above, the present invention relates to a method for manufacturing a bactericide consisting of an electrolytically treated liquid having high bactericidal action, characterized in introducing raw water containing hydrochloric acid to an electrolytic cell having no diaphragm between the cathode and anode, applying electrical power to the electrodes immersed in raw water containing hydrochloric acid, and recovering an electrolytically treated liquid, and relates to the manufacturing apparatus, and the bactericide that is manufactured by this method. The present invention has the following merits.

1) The manufacturing method and apparatus pertaining to the present invention allow the total amount of hydrochloric acid-containing raw water that is supplied to be used as a bactericide, making it unnecessary to discard the alkali ion water produced by the cathode and allowing the amounts of electrical power and water that are used to be reduced.

2) No diaphragm is used in the electrolytic cell in the manufacturing method and apparatus pertaining to the present invention, resulting in electrolytic cells and peripheral equipment that have a simple structure and lower diaphragm-related maintenance and control costs.

3) In the manufacturing method and apparatus pertaining to the present invention, the hydrochloric acid-containing raw water of low pH should be diluted after being electrolytically treated, so lower amounts of the water may be required in the treatment, and in this regard it is possible to make electrolytic cells and peripheral equipment that are smaller, that are less expensive, and that consume less energy.

4) The manufacturing method and apparatus pertaining to the present invention can prevent scale on the electrodes, resulting in longer operation and lower manufacturing costs.

5) The bactericide pertaining to the present invention consists of an electrolytically treated liquid having high bactericidal action, has high bactericidal effects, and can be used effectively to disinfect food manufacturing equipment and utensils, medical product manufacturing equipment and instruments, diagnostic tools, the hands of medical personnel, and the like.

6) The sterilizing method pertaining to the present invention can be used for an extremely broad range of raw water, and can be applied in a variety of fields, such as manufacturing activities, service activities, everyday activities, and the like.

7) According to the method of production of the present invention, a bactericide capable of being prepared at a higher electric power efficiency as compared with the prior application (WO97/17298) and containing no ozone but containing chlorine alone can be manufactured.

What is claimed as new and desired to be secured by Letters Patent of the United States is:

1. An economical method for manufacturing a bactericide, comprising an electrolytically treated liquid having bactericidal action and which contains essentially no ozone, comprising the steps of:
   a) preparing hydrochloric acid-containing raw water by adding chloride ion to the raw water, wherein the sole source of chloride ion which is added is in the form of hydrochloric acid having a molar concentration of between 0.001 mol/L and 6.4 mol/L;
   b) introducing the hydrochloric acid-containing raw water into an electrolytic cell having no diaphragm between the cathode and anode;
   c) applying an electric current between the cathode and anode such that the voltage between neighboring pair electrodes is between 1.3 volts and 3.9 volts, to thereby electrolyze the hydrochloric acid-containing raw water without causing wasteful oxygen or ozone, and then;
   d) recovering the liquid thus electrolytically treated.

2. The method according to claim 1, wherein the hydrochloric acid-containing raw water has a pH of between 0.5 and 3.0.

3. An economical method for manufacturing a bactericide, comprising an electrolytically treated liquid having bactericidal action and which contains essentially no ozone, comprising the steps of:
   a) preparing hydrochloride acid-containing raw water by adding chloride ion to the raw water, wherein the sole source of chloride ion which is added is in the form of hydrochloric acid having a molar concentration of between 0.001 mol/L and 6.4 mol/L;
   b) introducing the hydrochloric acid-containing raw water into electrolytic cells connected in series having no diaphragm between the cathode and anode;
   c) applying an electric current between the cathode and anode such that the voltage between neighboring pair electrodes is between 1.3 volts and 3.9 volts, to thereby electrolyze the hydrochloric acid-containing raw water without causing wasteful oxygen or ozone, and then;
   d) recovering the liquid thus electrolytically treated.

* * * * *